(12) United States Patent
Esenaliev et al.

(10) Patent No.: US 11,045,121 B2
(45) Date of Patent: *Jun. 29, 2021

(54) SYSTEMS AND METHODS FOR MEASURING OXYGENATION OR HEMOGLOBIN CONCENTRATION

(71) Applicants: Noninvasix, Inc., Galveston, TX (US); The Board of Regents of The University of Texas, Austin, TX (US)

(72) Inventors: Rinat Esenaliev, League City, TX (US); Donald S. Prough, Galveston, TX (US); Yuriy Petrov, Galveston, TX (US); Irene Petrov, Galveston, TX (US); George Saade, Houston, TX (US); Gayle L. Olson, Galveston, TX (US); Tommy G. Cooper, Friendswood, TX (US)

(73) Assignee: Noninvasix, Inc., Galveston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/253,678

(22) Filed: Jan. 22, 2019

(65) Prior Publication Data
US 2019/0216376 A1    Jul. 18, 2019

Related U.S. Application Data

(63) Continuation of application No. 14/794,037, filed on Jul. 8, 2015, now Pat. No. 10,231,656.
(Continued)

(51) Int. Cl.
*A61B 5/1455*    (2006.01)
*A61B 5/145*    (2006.01)
(Continued)

(52) U.S. Cl.
CPC ........ *A61B 5/14542* (2013.01); *A61B 5/0095* (2013.01); *A61B 5/1459* (2013.01);
(Continued)

(58) Field of Classification Search
USPC ........................................................ 600/310
See application file for complete search history.

(56) References Cited

U.S. PATENT DOCUMENTS

| | | |
|---|---|---|
| 4,537,197 A | 8/1985 | Hulka |
| 5,088,493 A | 2/1992 | Giannini et al. |

(Continued)

FOREIGN PATENT DOCUMENTS

| | | |
|---|---|---|
| DE | 4016234 A1 | 11/1990 |
| DE | 4400674 A1 | 7/1995 |

(Continued)

OTHER PUBLICATIONS

Al-Aweel, et al. Variations in prevalence of hypotension, hypertension, and vasopressor use in NICUs. J Perinatol. Jul.-Aug. 2001;21(5):272-8.
(Continued)

*Primary Examiner* — Eric F Winakur
*Assistant Examiner* — Marjan Fardanesh
(74) *Attorney, Agent, or Firm* — Wilson Sonsini Goodrich and Rosati, P.C.

(57) ABSTRACT

Optoacoustic diagnostic systems, devices, and methods are described. A system may comprise a console unit and a handheld probe. The console unit comprises a controller, a processor, a photodiode array, an acoustic processing subsystem, and a cooling subsystem. The probe directs light signals from the photodiode array to patient tissue. The light signals each have different wavelengths selected based on the physiological parameter of interest. The probe further comprises an acoustic transducer that receives acoustic
(Continued)

signals generated in response to the directed light signals. The probe may comprise a finger-held working end that can be directed to the skull of a fetus within the uterus during labor. The probe can then accurately determine blood oxygenation of the fetus to determine if a caesarian section is necessary.

16 Claims, 17 Drawing Sheets

Related U.S. Application Data

(60) Provisional application No. 62/021,946, filed on Jul. 8, 2014, provisional application No. 62/168,081, filed on May 29, 2015.

(51) Int. Cl.
  *A61B 5/00* (2006.01)
  *A61B 5/1464* (2006.01)
  *A61B 5/1459* (2006.01)

(52) U.S. Cl.
  CPC ........ *A61B 5/1464* (2013.01); *A61B 5/14551* (2013.01); *A61B 5/14553* (2013.01); *A61B 5/6814* (2013.01); *A61B 5/6875* (2013.01); *A61B 5/742* (2013.01); *A61B 2560/0425* (2013.01); *A61B 2562/0271* (2013.01)

(56) References Cited

U.S. PATENT DOCUMENTS

| | | | |
|---|---|---|---|
| 5,099,842 A | 3/1992 | Mannheimer et al. |
| 5,228,440 A | 7/1993 | Chung et al. |
| 5,348,002 A | 9/1994 | Caro |
| 5,377,673 A | 1/1995 | Van et al. |
| 5,823,952 A | 10/1998 | Levinson et al. |
| 5,840,023 A | 11/1998 | Oraevsky et al. |
| 5,897,503 A | 4/1999 | Lyon et al. |
| 5,941,821 A | 8/1999 | Chou |
| 6,049,728 A | 4/2000 | Chou |
| 6,309,352 B1 | 10/2001 | Oraevsky et al. |
| 6,381,480 B1 | 4/2002 | Stoddart et al. |
| 6,463,311 B1 | 10/2002 | Diab |
| 6,466,806 B1 | 10/2002 | Geva et al. |
| 6,484,044 B1 | 11/2002 | Lilienfeld-Toal |
| 6,498,942 B1 | 12/2002 | Esenaliev et al. |
| 6,553,242 B1 | 4/2003 | Sarussi |
| 6,567,678 B1 | 5/2003 | Oosta et al. |
| 6,594,515 B2 | 7/2003 | Watson |
| 6,725,073 B1 | 4/2004 | Motamedi et al. |
| 6,751,490 B2 | 6/2004 | Esenaliev et al. |
| 6,846,288 B2 | 1/2005 | Nagar et al. |
| 7,164,938 B2 | 1/2007 | Geddes et al. |
| 7,322,972 B2 | 1/2008 | Viator et al. |
| 7,430,445 B2 | 9/2008 | Esenal et al. |
| 7,515,948 B1 | 4/2009 | Balberg et al. |
| 7,747,301 B2 | 6/2010 | Cheng et al. |
| 7,916,283 B2 | 3/2011 | Fukutani et al. |
| 8,108,022 B2 | 1/2012 | Balberg et al. |
| 8,118,747 B2 | 2/2012 | Furia et al. |
| 8,121,663 B2 | 2/2012 | Peyman et al. |
| 8,200,305 B2 | 6/2012 | Hwang |
| 8,280,469 B2 | 10/2012 | Baker et al. |
| 8,332,006 B2 | 12/2012 | Naganuma et al. |
| 8,352,005 B2 | 1/2013 | Esenaliev et al. |
| 8,423,111 B2 | 4/2013 | Fujiwara |
| 8,501,099 B2 | 8/2013 | Viator et al. |
| 8,781,548 B2 | 7/2014 | Besko et al. |
| 8,852,095 B2 | 10/2014 | Schlottau et al. |
| 8,864,667 B2 | 10/2014 | Asao et al. |
| 8,885,155 B2 | 11/2014 | Li et al. |
| 8,930,145 B2 | 1/2015 | Li et al. |
| 8,934,953 B2 | 1/2015 | Carr et al. |
| 9,259,176 B2 | 2/2016 | Suzuki |
| 9,380,967 B2 | 7/2016 | Esenaliev et al. |
| 10,231,656 B2 | 3/2019 | Esenaliev et al. |
| 2002/0137996 A1 | 9/2002 | Chung et al. |
| 2002/0137997 A1 | 9/2002 | Mastrototaro et al. |
| 2006/0100530 A1 | 5/2006 | Kliot et al. |
| 2006/0173331 A1 | 8/2006 | Booton et al. |
| 2006/0184042 A1 | 8/2006 | Wang et al. |
| 2007/0015992 A1 | 1/2007 | Filkins et al. |
| 2008/0255433 A1 | 10/2008 | Prough et al. |
| 2009/0069652 A1 | 3/2009 | Lee et al. |
| 2009/0108205 A1 | 4/2009 | Duffy et al. |
| 2010/0081904 A1 | 4/2010 | Medina |
| 2011/0118576 A1 | 5/2011 | Eghtesady et al. |
| 2011/0239766 A1 | 10/2011 | Nakajima et al. |
| 2012/0300024 A1* | 11/2012 | McEldowney ......... G06F 3/011 348/42 |
| 2013/0102865 A1 | 4/2013 | Mandelis et al. |
| 2013/0112001 A1 | 5/2013 | Furukawa |
| 2013/0150749 A1 | 6/2013 | McLean et al. |
| 2013/0190589 A1 | 7/2013 | Chen et al. |
| 2013/0324815 A1 | 12/2013 | Jian et al. |
| 2014/0142404 A1 | 5/2014 | Wang et al. |
| 2014/0275943 A1 | 9/2014 | Kang et al. |
| 2014/0343384 A1 | 11/2014 | Floyd et al. |
| 2014/0378811 A1 | 12/2014 | Nanaumi |
| 2015/0051473 A1 | 2/2015 | Huang et al. |
| 2015/0099973 A1 | 4/2015 | Abe |
| 2016/0007892 A1 | 1/2016 | Esenaliev et al. |

FOREIGN PATENT DOCUMENTS

| | | |
|---|---|---|
| JP | 6090535 | 5/1985 |
| JP | 2006326223 A | 12/2006 |
| JP | 4226639 B1 | 2/2009 |
| JP | 2009526707 A | 7/2009 |
| JP | 2011083531 A | 4/2011 |
| WO | WO-2012066930 A1 | 5/2012 |

OTHER PUBLICATIONS

Bassan. Intracranial hemorrhage in the preterm infant: understanding it, preventing it. Clin Perinatol. Dec. 2009;36(4):737-62, v. doi: 10.1016/j.clp.2009.07.014.
Basu, et al. Cerebral blood flow velocity in early-onset neonatal sepsis and its clinical significance. Eur J Pediatr. Jun. 2012;171(6):901-9. doi: 10.1007/s00431-011-1643-y. Epub Jan. 4, 2012.
Benders, et al. Phase-contrast magnetic resonance angiography measurements of global cerebral blood flow in the neonate. Pediatr Res. Jun. 2011;69(6):544-7. doi: 10.1203/PDR.0b013e3182176aab.
Biomedical Photonics Handbook. CRS Press, 2003. 22 pages.
Bode, et al. Age dependence of flow velocities in basal cerebral arteries. Arch Dis Child. Jun. 1988;63(6):606-11.
Booth, et al. Near-infrared spectroscopy monitoring of cerebral oxygen during assisted ventilation. Surg Neurol Int. 2011;2:65. doi: 10.4103/2152-7806.81722. Epub May 28, 2011.
Brecht, et al. In vivo monitoring of blood oxygenation in large veins with a triple-wavelength optoacoustic system. Opt Express. Nov. 26, 2007;15(24):16261-9.
Caravale, et al. Change in cognitive abilities over time during preschool age in low risk preterm children. Early Hum Dev. Jun. 2012;88(6):363-7. doi: 10.1016/j.earlhumdev.2011.09.011. Epub Nov. 1, 2011.
Deeg, et al. Pulsed Doppler sonographic measurement of normal values for the flow velocities in the intracranial arteries of healthy newborns. Pediatr Radiol. 1989;19(2):71-8.
EP15818510.8 Extended Search Report dated Feb. 15, 2018.
Esenaliev, et al. Axial resolution of laser optoacoustic imaging: Influence of acoustic attenuation and diffraction. SPIE Proc 1998; 3254: 294-301.
Esenaliev, et al. Laser optoacoustic imaging for breast cancer diagnostics: limit of detection and comparison with x-ray and ultrasound imaging. Proc SPIE 1997; 2979: 71-82.
Esenaliev, et al. Optoacoustic technique for non-invasive, real-time monitoring of cerebral blood oxygenation. LEOS Proc 2001; 192-3.

(56) References Cited

OTHER PUBLICATIONS

Esenaliev, et al. Studies of acoustical and shock waves in the pulsed laser ablation of biotissue. Lasers Surg Med. 1993;13(4):470-84.

Esenaliev RO, Larina IV, Larin KV, Deyo DJ, Motamedi M, Prough DS "Optoacoustic Technique for Noninvasive Monitoring of Blood Oxygenation: A Feasibility Study" Applied Optics (2002) 41:4722-31.

Fanaroff, et al. Blood pressure disorders in the neonate: hypotension and hypertension. Semin Fetal Neonatal Med. Jun. 2006;11(3):174-81. Epub Mar. 3, 2006.

Fauchere, et al. Near-infrared spectroscopy measurements of cerebral oxygenation in newborns during immediate postnatal adaptation. J Pediatr. Mar. 2010;156(3):372-6. doi: 10.1016/j.jpeds.2009.09.050. Epub Nov. 14, 2009.

"Final Office action dated Aug. 29, 2018 for U.S. Appl. No. 14/794,022".

Friedrich, et al., Quantitative photoacoustic blood oxygenation measurement of whole porcine blood samples using a multi-wavelength semiconductor laser system. Diffuse Optical Imaging III, SPIE, 1000 20th st. Belligham WA 98225-6705, USA, Jun. 9, 2011; 8088(1):1-9.

Gilmore, et al. Relationship between cerebrovascular dysautoregulation and arterial blood pressure in the premature infant. J Perinatol. Nov. 2011;31(11):722-9. doi: 10.1038/jp.2011.17. Epub Mar. 3, 2011.

Gusev, et al. Laser Optoacoustics. New York, American Institute of Physics Press, 1993. 4 pages.

Heldt, et al. Continuous quantitative monitoring of cerebral oxygen metabolism in neonates by ventilator-gated analysis of NIRS recordings. Acta Neurochir Suppl. 2012;114:177-80. doi: 10.1007/978-3-7091-0956-4_34.

Honda, et al. Effect of therapeutic touch on brain activation of preterm infants in response to sensory punctate stimulus: a near-infrared spectroscopy-based study. Arch Dis Child Fetal Neonatal Ed. May 2013;98(3):F244-8. doi: 10.1136/archdischild-2011-301469. Epub Jul. 21, 2012.

Iadecola, et al. Glial regulation of the cerebral microvasculature. Nat Neurosci. Nov. 2007;10(11):1369-76.

International search report and written opinion dated Dec. 8, 2015 for PCT/US2015/039620.

Kehrer, et al. Development of cerebral blood flow volume in preterm neonates during the first two weeks of life. Pediatr Res. Nov. 2005;58(5):927-30. Epub Sep. 23, 2005.

Kehrer, et al. Measurement of volume of cerebral blood flow in healthy preterm and term neonates with ultrasound. Lancet. Nov. 30, 2002;360(9347):1749-50.

Kennedy, et al. An adaptation of the nitrous oxide method to the study of the cerebral circulation in children; normal values for cerebral blood flow and cerebral metabolic rate in childhood. J Clin Invest. Jul. 1957;36(7):1130-7.

Kissack, et al. Postnatal changes in cerebral oxygen extraction in the preterm infant are associated with intraventricular hemorrhage and hemorrhagic parenchymal infarction but not periventricular leukomalacia. Pediatr Res. Jul. 2004;56(1):111-6. Epub May 19, 2004.

Larin, et al. Comparison of Optoacoustic Tomography with Ultrasound and X-ray imaging for Breast Cancer Detection. SPIE Proc. 2001; 4256: 147-53.

Munro, et al. Hypotensive extremely low birth weight infants have reduced cerebral blood flow. Pediatrics. Dec. 2004;114(6):1591-6.

Niwa, et al. Anatomic dependency of phase shifts in the cerebral venous system of neonates at susceptibility-weighted MRI. J Magn Reson Imaging. Nov. 2011;34(5):1031-6. doi: 10.1002/jmri.22782. Epub Aug. 23, 2011.

Noori, et al. Systemic and cerebral hemodynamics during the transitional period after premature birth. Clin Perinatol. Dec. 2009;36(4):723-36, v. doi: 10.1016/j.clp.2009.07.015.

Notice of allowance dated Apr. 13, 2016 for U.S. Appl. No. 14/793,969.

Office action dated Nov. 20, 2015 for U.S. Appl. No. 14/793,969.

Oraevsky, et al. Breast cancer diagnostics by laser opto-acoustic tomography. Advances in Optical Imaging and Photon Migration. Edited by Alfano RR, Fujimoto JG. OSA Publishing House, 1996, pp. 316-321.

Oraevsky, et al. Laser optic-acoustic tomography for medical diagnostics: principles. Proc SPIE 1996; 2676: 22-31.

Oraevsky, et al. Laser-based optoacoustic imaging in biological tissues. Proc SPIE, Laser Tissue Interation V. 1994; 2134: 122-8.

Oraevsky, et al. Two-dimensional opto-acoustic tomography transducer array and image reconstruction algorithm. SPIE Proc 1999; 3601: 256-67.

Patrikeev, et al. Signal processing of optoacoustic transients for monitoring of total hemoglobin concentration and oxygenation in blood vessels. SPIE Photonics West. BiOS 2007. Conference 6437. Abstract 6437.43.

Patrikeev, et al. Wavelet differentiation of optoacoustic signals for monitoring of total hemoglobin concentration and oxygen saturation level in small blood vessels. Proc. SPIE 2007; 6437, 643717 (Feb. 13, 2007); doi:10.1117/12.714185.

Petrov, et al. Clinical tests of noninvasive, optoacoustic, cerebral venous oxygenation monitoring system. Photons Plus Ultrasound: Imaging and Sensing 2009, edited by Alexander A. Oraevsky, Lihong V. Wang, Proc. of SPIE vol. 7177, 717706.2009.

Petrov, et al. Monitoring cerebral venous blood oxygentation in neonates with a medical-grade optoacoustic system. Proc. of SPIE. 2015; vol. 9323:932302. doi: 10.1117/12.2085076.

Petrov, et al. Multiwavelength optoacoustic system for noninvasive monitoring of cerebral venous oxygenation: a pilot clinical test in the internal jugular vein. Opt Lett. Jun. 15, 2006;31(12):1827-9.

Petrov, et al. Noninvasive optoacoustic monitoring of cerebral venous blood oxygenation in newborns. Proc. SPIE 8223, Photons Plus Ultrasound: Imaging and Sensing 2012, 82231M (Feb. 9, 2012)).

Petrov, et al. Optoacoustic monitoring of cerebral venous blood oxygenation though intact scalp in large animals. Opt Express. Feb. 13, 2012;20(4):4159-67. doi: 10.1364/OE.20.004159.

Petrov, et al. Optoacoustic, noninvasive, real-time, continuous monitoring of cerebral blood oxygenation: an in vivo study in sheep. Anesthesiology. Jan. 2005;102(1):69-75.

Petrova, et al. Noninvasive monitoring of cerebral blood oxygenation in ovine superior sagittal sinus with novel multi-wavelength optoacoustic system. Opt Express. Apr. 27, 2009;17(9):7285-94.

Pollard, et al. The influence of carbon dioxide and body position on near-infrared spectroscopic assessment of cerebral hemoglobin oxygen saturation. Anesth Analg. Feb. 1996;82(2):278-87.

Pryds, et al. Heterogeneity of cerebral vasoreactivity in preterm infants supported by mechanical ventilation. J Pediatr. Oct. 1989;115(4):638-45.

Reynolds, et al. Spectral pattern of neonatal cerebral blood flow velocity: comparison with spectra from blood pressure and heart rate. Pediatr Res. Feb. 1997;41(2):276-84.

Robertson, et al. Prevention of secondary ischemic insults after severe head injury. Crit Care Med. Oct. 1999;27(10):2086-95.

Roggan, et al. Optical Properties of Circulating Human Blood in the Wavelength Range 400-2500 nm. J Biomed Opt. Jan. 1999;4(1):36-46.

Sorensen, et al. The brains of very preterm newborns in clinically stable condition may be hyperoxygenated. Pediatrics. Nov. 2009;124(5):e958-63. doi: 10.1542/peds.2008-2394. Epub Oct. 19, 2009.

Soul, et al. CSF removal in infantile posthemorrhagic hydrocephalus results in significant improvement in cerebral hemodynamics. Pediatr Res. May 2004;55(5):872-6. Epub Jan. 22, 2004.

Soul, et al. Fluctuating pressure-passivity is common in the cerebral circulation of sick premature infants. Pediatr Res. Apr. 2007;61(4):467-73.

Takahashi, et al. Developmental changes of cerebral blood flow and oxygen metabolism in children. AJNR Am J Neuroradiol. May 1999;20(5):917-22.

Tsuji, et al. Cerebral intravascular oxygenation correlates with mean arterial pressure in critically ill premature infants. Pediatrics. Oct. 2000;106(4):625-32.

U.S. Appl. No. 14/794,022, Office Action dated Apr. 6, 2018.

(56) References Cited

OTHER PUBLICATIONS

U.S. Appl. No. 14/794,037, Office Action dated Mar. 26, 2018.
Varela, et al. Mean cerebral blood flow measurements using phase contrast MRI in the first year of life. NMR Biomed. Sep. 2012;25(9):1063-72. doi: 10.1002/nbm.2771. Epub Jan. 31, 2012.
Volpe. Brain injury in premature infants: a complex amalgam of destructive and developmental disturbances. Lancet Neurol. Jan. 2009;8(1):110-24. doi: 10.1016/S1474-4422(08)70294-1.
Welch, et al. Optical-thermal response of laser-irradiated tissue. New York, Plenum Press, 1995. 13 pages.
Wintermark, et al. Brain perfusion in asphyxiated newborns treated with therapeutic hypothermia. AJNR Am J Neuroradiol. Dec. 2011;32(11):2023-9. doi: 10.3174/ajnr.A2708. Epub Oct. 6, 2011.
Wintermark, et al. Brain perfusion in children: evolution with age assessed by quantitative perfusion computed tomography. Pediatrics. Jun. 2004;113(6):1642-52.
Wong, et al. Impaired autoregulation in preterm infants identified by using spatially resolved spectroscopy. Pediatrics. Mar. 2008;121(3):e604-11. doi: 10.1542/peds.2007-1487. Epub Feb. 4, 2008.
Wray, et al. Characterization of the near infrared absorption spectra of cytochrome aa3 and haemoglobin for the non-invasive monitoring of cerebral oxygenation. Biochim Biophys Acta. Mar. 30, 1988;933(1):184-92.
Wynne, et al. Optoacoustic Monitoring of Oxygen Saturation in the Superior Sagittal Sinus of Neonates (Abstract A676). American Society of Anesthesiologists. Oct. 16, 2011.

\* cited by examiner

SYSTEMS AND METHODS FOR MEASURING OXYGENATION OR HEMOGLOBIN CONCENTRATION

CROSS-REFERENCE

This application is a continuation U.S. patent application Ser. No. 14/794,037, filed Jul. 8, 2015, now U.S. Pat. No. 10,231,656, which claims the benefit of U.S. Provisional Application Nos. 62/021,946, filed Jul. 8, 2014, and 62/168,081, filed May 29, 2015, the full disclosures of which are incorporated herein by reference.

The subject matter of this application is related to the subject matter of the following patents and patent applications: U.S. Pat. No. 6,309,352, issued Oct. 27, 1998 and entitled "Real Time Optoacoustic Monitoring of Changes in Tissue Properties," U.S. Pat. No. 6,498,942, issued Dec. 24, 2002 and entitled "Optoacoustic Monitoring of Blood Oxygenation," U.S. Pat. No. 6,725,073, issued Apr. 20, 2004 and entitled "Methods for Noninvasive Analyte Sensing," U.S. Pat. No. 6,751,490, issued Jun. 15, 2004 and entitled "Continuous Optoacoustic Monitoring of Hemoglobin Concentration and Hematocrit," U.S. Pat. No. 7,430,445, issued Sep. 30, 2008 and entitled "Noninvasive Blood Analysis by Optical Probing of the Veins Under the Tongue," U.S. Pat. No. 8,135,460, issued Mar. 13, 2012 and entitled "Noninvasive Glucose Sensing Methods and Systems," U.S. Pat. No. 8,352,005, issued Jan. 8, 2013 and entitled "Noninvasive Blood Analysis by Optical Probing of the Veins Under the Tongue," and U.S. Pat. No. 9,380,967, issued Jul. 5, 2016 and entitled "Systems and Methods for Measuring Cerebral Oxygenation," and U.S. patent application Ser. No. 12/101,891, filed Apr. 11, 2007 and entitled "Optoacoustic Monitoring of Multiple Parameters," Ser. No. 13/538,687, filed Jun. 29, 2012 and entitled "Noninvasive, Accurate Glucose Monitoring with OCT by using Tissue Warming and Temperature Control," and Ser. No. 14/794,022, filed Jul. 8, 2015 and entitled "Systems and Methods for Measuring Oxygenation," the full disclosures of which are fully incorporated herein by reference.

NOTICE OF GOVERNMENT-SPONSORED RESEARCH

This invention was made with Government support under grant/contract number 1R43HD075551-01, awarded by the National Institutes of Health (NIH). The Government has certain rights in the invention.

BACKGROUND

Cerebral hypoxia during labor represents a risk factor for death or severe neurologic complications (e.g., cerebral palsy). At present, there are no commercially available monitors that can be used to detect cerebral hypoxia, other than fetal heart rate (FHR) monitors that use changes in basal heart rate and changes in FHR variability and timing of FHR decelerations to indirectly assess fetal asphyxia. Although fetal heart rate monitoring provides important information regarding fetal oxygenation, this information is somewhat limited and provides no information regarding the risk of cerebral palsy. As a consequence, many cesarean sections are performed as a defensive measure to reduce the risk of intrapartum fetal asphyxia by reducing the duration of labor. Unfortunately, defensive cesarean sections entail added maternal risk. Maternal death rates are 21% higher in states with cesarean section rates exceeding 33% than those with rates less than 33%.

In view of the limited information provided by FHR and the risks associated with cesarean procedures, it can be appreciated that it would be desirable to have a more direct way of measuring fetal cerebral oxygenation (i.e., hemoglobin saturation).

References that may be of interest include: U.S. Pat. Nos. 4,537,197, 5,088,493, 5,099,842, 5,228,440, 5,348,002, 5,377,673, 5,823,952, 5,840,023, 5,941,821, 6,049,728, 6,381,480, 6,553,242, 6,594,515, 6,463,311, 6,466,806, 6,484,044, 6,567,678, 6,751,490, 6,846,288, 7,164,938, 7,322,972, 7,515,948, 7,747,301, 7,916,283, 8,121,663, 8,280,469, 8,332,006, 8,423,111, 8,501,099, 8,781,548, 8,852,095, 8,864,667, 8,885,155, 8,930,145, and 8,934,953; U.S. Publication Nos. 2006/100530, 2006/184042, 2007/015992, 2009/069652, 2009/108205, 2010/081904, 2011/239766, 2013/112001, 2013/190589, 2013/324815, 2014/142404, 2014/275943, 2014/343384, 2014/378811, 2015/051473, and 2015/099973; German Patent Publication No. DE 4400674 A1; and, "Noninvasive monitoring of cerebral blood oxygenation in ovine superior sagittal sinus with novel multi-wavelength optoacoustic system" to Petrova et al. (27 Apr. 2009/Vol. 17, No. 9/OPTICS EXPRESS 7285).

SUMMARY

The present disclosure relates generally to medical devices and methods for their use, and particularly optoacoustic diagnostic devices and methods. Systems, devices, and methods to determine one or more physiological parameters optoacoustically are described. An exemplary system may comprise a convenient, desktop-sized console unit comprising a controller and/or a processor, a photodiode array, an acoustic processing subsystem, and a cooling subsystem. The system may further comprise a handheld probe that can be coupled to the console unit. The probe may direct light signals from the photodiode array of the console unit to patient tissue. A plurality of light signals, each having different wavelengths, may be directed to the tissue. The wavelengths of the light may be selected based on the physiological parameter(s) of interest. The probe may further comprise an acoustic transducer that receives acoustic signals generated in response to the directed light signals. The probe may have various form factors. For example, the probe may comprise a finger-held working end that can be directed to the skull of a fetus within the uterus during labor. The probe can then accurately determine blood oxygenation of the fetus to determine if a caesarian procedure is necessary, thereby improving outcomes for the mother and child during labor and reducing malpractice lawsuits and premiums. The console unit can show the blood oxygenation levels (and/or other physiological parameter(s)) of the fetus or other target tissue and communicate with other computerized healthcare systems, such as electronic health care records, to record and analyze blood oxygenation readings or other measured physiological parameters.

Aspects of the present disclosure provide apparatuses, such as a desktop-sized console, for monitoring oxygenation of a subject. The console may comprise a laser diode subsystem for emitting light pulses directed to tissue of a subject and an acoustic sensor subsystem for measuring acoustic pressure generated in the tissue in response to the emitted light pulses. The laser diode subsystem may comprise a first laser diode with a first laser diode driver, a first temperature controller with a first thermoelectric cooler and a first temperature sensor, a second laser diode, a second temperature controller with a second thermoelectric cooler and a second temperature sensor, a first cooling fan, and a laser controller. The first laser diode may be configured to emit a first light pulse having a first wavelength. The first thermoelectric cooler may be coupled to the first laser diode to add or remove heat to regulate a temperature of the first laser diode, which may be detected by the first temperature sensor. The second laser diode may be configured to emit a second light pulse having a second wavelength different from the first wavelength. The second thermoelectric cooler may be coupled to the second laser diode to add or remove heat to regulate a temperature of the second laser diode, which may be detected by the second temperature sensor. The first and second temperature controllers may be coupled to the first cooling fan and the first and second thermoelectric coolers to control the first cooling fan, the first thermoelectric cooler, and the second thermoelectric cooler to regulate the temperatures of the first and second laser diodes. The first and second temperature controllers may be configured to keep the first and second laser diodes in an optimal temperature range such that the first and second laser diodes can consistently emit light pulses at the desired wavelengths. Oxygenation of the subject may be determined in response to the received acoustic pressure.

The laser diode subsystem may further comprise a third laser diode and a third temperature controller, which may comprise a third temperature sensor and a third thermoelectric cooler. The third laser diode may be configured to emit a third light pulse having a third wavelength different from the first and second wavelengths. The third thermoelectric cooler may be coupled to the third laser diode to regulate a temperature of the third laser diode. The third temperature sensor may be further coupled to the third thermoelectric cooler to regulate the temperature of the third laser diode.

The first temperature controller may comprise the first thermoelectric cooler and the first temperature sensor to measure and control the temperature of the first laser diode. The second thermoelectric controller may comprise a second thermoelectric cooler and a second temperature sensor to measure and control the temperature of the second laser diode. And, the third temperature controller may comprise the third thermoelectric cooler and the third temperature sensor to measure and control the temperature of the third laser diode. The first, second, and/or third temperature controllers may be configured to regulate the temperatures of the first, second, and/or third laser diodes in response to the temperatures measured by the first, second, and third temperature sensors, respectively. The first, second, or third wavelength may be in a range of 685 nm to 715 nm, 715 nm to 745 nm, 745 nm to 775 nm, 790 nm to 820 nm, or 845 nm to 875 nm.

The console may further comprise a processor coupled to the laser diode subsystem to control the laser diode subsystem and coupled to the acoustic sensor subsystem to receive the measured acoustic pressure. The processor may be configured to determine oxygenation of the subject in response to the measured acoustic pressure. The console may further comprise a power supply coupled to the laser diode subsystem, the acoustic sensor subsystem, and the processor. The console may further comprise a display coupled to the processor to display the determined oxygenation to a user. The display may comprise a touch screen for operating the console. The console may further comprise a desktop-sized housing enclosing the laser diode subsystem, the acoustic sensor subsystem, and the processor. The console may further comprise a second cooling fan, which may be coupled to one or more of the processor or acoustic sensor subsystem, for cooling the console. The processor may be capable of accessing medical records of the subject.

The console may further comprise an output port for the laser diode subsystem and an input port for the acoustic sensor subsystem. The output port and the input port may be configured to be coupled to a sensor module or an optoacoustic probe to emit the one or more light pulses to the tissue of the subject and to receive the acoustic pressure generated in the tissue. The output port and the input port may be configured to be coupled to the sensor module or optoacoustic probe with a cable comprising one or more optical fibers.

Aspects of the present disclosure also provide methods of monitoring oxygenation of a subject. A first light pulse having a first wavelength may be generated with a first laser diode. A second light pulse having a second wavelength different from the first wavelength may be generated with a second laser diode. The temperatures of the first and second laser diodes may be regulated with a first thermoelectric cooler coupled to the first laser diode, a second thermoelectric cooler coupled to the second laser diode, and/or a first cooling fan. The generated first and second light pulses may be directed to tissue of a subject. Acoustic pressure generated in the tissue in response to the directed first and second light pulses may be measured. Oxygenation of the subject may be determined in response to the measured acoustic pressure.

A third light pulse having a third wavelength different from the first and second wavelengths may be generated with a third laser diode. A temperature of the third laser diode may be regulated with a third thermoelectric cooler coupled to the third laser diode and the first cooling fan. The generated third light pulse may be directed to the tissue of the subject. The measured acoustic pressure may be generated in the tissue in response to the directed first, second, and third light pulses.

The first temperature controller may comprise a first temperature sensor to measure the temperature of the first laser diode and a first thermoelectric cooler to add or remove heat to regulate the temperature of the first laser diode in response to the measured temperature. The second temperature controller may comprise a second temperature sensor to measure the temperature of the second laser diode and a second thermoelectric cooler to add or remove heat to regulate the temperature of the second laser diode in response to the measured temperature. And, the third temperature controller may comprise a third temperature sensor to measure the temperature of the third laser diode and a third thermoelectric cooler to add or remove heat to regulate the temperature of the third laser diode in response to the measured temperature. The first, second, and third temperature controllers may be configured to regulate the temperatures of the first, second, and third laser diodes in response to the temperatures measured by the first, second, and third temperature sensors, respectively. The first, second, or third wavelength may be in a range of 685 nm to 715 nm, 715 nm to 745 nm, 745 nm to 775 nm, 790 nm to 820 nm, or 845 nm to 875 nm.

The determined oxygenation of the subject may be displayed. The temperatures of the first, second, and/or third laser diodes may be regulated with a second cooling fan. The second cooling fan may be enclosed within a housing enclosing the first laser diode, the second laser diode, the third laser diode, and/or the first cooling fan. The generated first and second light pulses may be directed to tissue of the subject by directing the first and second light pulses with an optical waveguide of a sensor module or an optoacoustic sensor coupled to the first and second photodiodes. The acoustic pressure may be measured by an acoustic transducer of the sensor module or the optoacoustic sensor.

Aspects of the present disclosure also provide methods for optoacoustically determining oxygenation of a subject. A first light having a first wavelength may be emitted to tissue of the subject. A second light having a second wavelength may be emitted to the tissue. The second wavelength may be different from the first wavelength. A third light having a third wavelength may be emitted to the tissue. The third wavelength may be different from the first and second wavelengths. Acoustic pressure generated by the tissue in response to the first, second, and third emitted lights may be detected.

The first wavelength may be in a range from 790 to 820 nm, such as 800 nm or 805 nm. The second or third wavelength may be in a range from 685 nm to 715 nm, 715 nm to 745 nm, 745 nm to 775 nm, or 845 nm to 875 nm, such as 700 nm, 730 nm, 760 nm, or 860 nm, for example.

The first, second, and third lights may be emitted from a common light source. The common light source may be configured to rapidly switch between emitting the first light with the first wavelength, the second light with the second wavelength, and the third light with the third wavelength. For example, the common light source may be a commonly controlled laser diode array or an optical parametric oscillator (OPO). The first, second, and third lights may be emitted to the tissue from a common optical fiber.

One or more of the first, second, or third lights may have an energy level of at least 0.5 microjoules. One or more of the emitted first, second, or third lights may have a pulse width of at least 100 ns. One or more of the emitted first, second, or third lights may have a repetition rate of 10 to 10,000 Hz.

Oxygenation may be determined in response to the detected acoustic pressure by determining oxygenation in response to a first difference in detected acoustic pressure in response to the first emitted light and in response to the second emitted light and a second difference in detected acoustic pressure in response to the first emitted light and in response to the third emitted light. Oxygenation may be determined by determining oxygenation in response to an average of oxygenation determined in response to the first difference and oxygenation determined in response to the second difference. The first wavelength may have substantially equal absorption between oxyhemoglobin and deoxyhemoglobin. The second and third wavelengths may have absorption differences between oxyhemoglobin and deoxyhemoglobin.

Aspects of the present disclosure also provide systems for optoacoustically determining oxygenation of a subject. The system may further comprise a light source, an acoustic transducer, and a processor. The light source may be configured to emit to tissue a first light having a first wavelength, a second light having a second wavelength different from the second wavelength, and a third light having a third wavelength different from the first and second wavelengths. The acoustic transducer may be configured to detect acoustic pressure generated by the tissue in response to the first, second, and third emitted lights. The processor may be configured to determine oxygenation in response to the detected acoustic pressure.

The light source may comprise an array of laser diodes or light emitting diodes. The array of laser diodes or light emitting diodes may comprise a first laser diode configured to emit the first light, a second laser diode configured to emit the second light, and a third laser diode configured to emit the third light. The first wavelength may be in a range from 790 to 820 nm, such as 805 nm. The second or third wavelength may be in a range from 685 nm to 715 nm, 715 nm to 745 nm, 745 nm to 775 nm, or 845 nm to 875 nm, such as 700 nm, 730 nm, 760 nm, or 860 nm, for example.

The system may further comprise a controller configured to rapidly switch the light source between emitting the first light with the first wavelength, the second light with the second wavelength, and the third light with the third wavelength. For example, the light source may be a commonly controlled laser diode array or an optical parametric oscillator (OPO). The first, second, and third lights may be emitted to the tissue from a common optical fiber.

One or more of the first, second, or third lights may have an energy level of at least 0.5 microjoules. One or more of the emitted first, second, or third light may have a pulse width of at least 150 ns. One or more of the emitted first, second, or third light may have a repetition rate of 10 to 2000 Hz.

The processor may be configured to determine oxygenation in response to a first difference in detected acoustic pressure in response to the first emitted light and in response to the second emitted light and a second difference in detected acoustic pressure in response to the first emitted light and in response to the third emitted light. The processor may be configured to determine oxygenation in response to an average of oxygenation determined in response to the first difference and oxygenation determined in response to the second difference. The first wavelength may have substantially equal absorption between oxyhemoglobin and deoxyhemoglobin. The second and third wavelengths may have absorption differences between oxyhemoglobin and deoxyhemoglobin. The system may further comprise a display configured to display the determined oxygenation.

Aspects of the present disclosure may also provide methods of monitoring oxygenation of a fetus, such as venous oxygenation of the fetus. A sensor may be inserted into a vagina. The sensor may comprise a light output and an acoustic transducer. The sensor may be advanced through a cervix and into a uterus. The sensor may be positioned over a head of the fetus. The light output of the sensor may emit light to the head of the fetus and the acoustic transducer of the sensor may detect acoustic pressure generated in response to the emitted light. The sensor may determine oxygenation of the fetus in response to the detected acoustic pressure.

The sensor may comprise a probe head, which may be inserted into the vagina. The sensor may comprise an oxygenation monitor configured to display the determined oxygenation of the fetus and a cable connecting the probe head with the oxygenation monitor. The oxygenation monitor and at least a portion of the cable may remain outside the uterus as the probe head is inserted into the vagina. The light output may comprise a waveguide in the probe head. The cable may comprise one or more optical fibers and the oxygenation monitor may comprise one or more laser diodes or light emitting diodes coupled to the waveguide through the one or more optical fibers. To insert the sensor into the vagina, the probe head may be grasped between two finger tips of a user. The sensor may be positioned over a head of the fetus by positioning the light output and the acoustic transducer to face a superior sagittal sinus of the fetus. To position the sensor over a head of the fetus comprises, a tip of the light output extending from the probe head may be contacted with skin of the head of the fetus, such as to pass through hair to reduce loss of light intensity due to absorption by the hair.

The light output of the sensor may emit light to a superior sagittal sinus of the fetus. The acoustic pressure generated in response to the emitted light may be generated by the superior sagittal sinus. The sensor may determine oxygenation of the superior sagittal sinus. The sensor may be inserted into the vagina/birth canal and uterus during labor.

The light emitted by the light output may have an energy of 1 μJ to 1 mJ. The light emitted by the light output may have wavelengths in range of two or more of 685-715 nm, 715-745 nm, 745-775 nm, 790-820 nm, or 845-875 nm, such as wavelengths in range of two or more of 700 nm, 730 nm, 760 nm, 805 nm, or 860 nm.

Aspects of the present disclosure may also provide further methods of monitoring oxygenation of a fetus, such as venous oxygenation of the fetus. Light may be emitted from a light output of a sensor positioned over a head of a fetus in a uterus. Acoustic pressure may be detected with an acoustic transducer of the sensor. The acoustic pressure may be generated in response to the emitted light. Oxygenation of the fetus may be determined in response to the detected acoustic pressure. The determined oxygenation of the fetus may be displayed to the user with the sensor.

The sensor may comprise a probe head comprising the light output and acoustic transducer. The light output may comprise a tip extending out from a housing of the probe head. The sensor may comprise an oxygenation monitor configured to display the determined oxygenation of the fetus and a cable connecting the probe head with the oxygenation monitor. The light output may comprise a waveguide, such as an optical fiber, in the probe head. The cable may comprise one or more optical fibers and/or electrical cables. The oxygenation monitor may comprise one or more laser diodes or light emitting diodes coupled to the waveguide through the one or more optical fibers and/or other optical components such as mirrors or lenses. The electrical cable(s) may connect the acoustic transducer in the probe head to the oxygenation monitor.

The light output and the acoustic transducer may be positioned to face a superior sagittal sinus of the fetus. The light output of the sensor may emit light to a superior sagittal sinus of the fetus. The acoustic pressure generated in response to the emitted light may be generated by blood in the superior sagittal sinus. The sensor may determine the oxygenation of venous blood in the superior sagittal sinus.

The light emitted by the light output may have an energy of 1 μJ to 1 mJ. The light emitted by the light output may have wavelengths in range of two or more of 685-715 nm, 715-745 nm, 745-775 nm, 790-820 nm, or 845-875 nm, such as wavelengths in range of two or more of 700 nm, 730 nm, 760 nm, 800 nm, 805 nm, or 860 nm.

Aspects of the present disclosure also provide systems for monitoring oxygenation of a fetus, such as venous cerebral oxygenation of the fetus. The system may comprise a monitor, a cable, and a probe head. The monitor may comprise a processor, a light source, and a display. The probe head may be configured to be held between two finger tips of a user and coupled to the monitor through the cable. The probe head may comprise a light output and an acoustic transducer. The light source may be configured to generate a light emitted to the fetus through the light output of the probe head. The acoustic transducer may be configured to detect acoustic pressure generated in response to the emitted light. The processor may be configured to determine oxygenation of the fetus in response to the detected acoustic pressure. The display may be configured to display the determined oxygenation. The light output may comprise a tip extending out from a housing of the probe head.

The light source of the monitor may comprise one or more laser diodes or light emitting diodes. The light source of the monitor may be configured to generate light having an energy of 1 μJ to 1 mJ. The light source of the monitor may be configured to generate light having wavelengths in range of two or more of 685-715 nm, 715-745 nm, 745-775 nm, 790-820 nm, or 845-875 nm, such as two or more of 700 nm, 730 nm, 760 nm, 800 nm, 805 nm, or 860 nm, for example. The cable may comprise one or more optical fibers configured to direct light generated by the light source to the light output of the probe head.

Aspects of the present disclosure may also provide fetal cerebral venous oxygenation probes. A fetal cerebral venous oxygenation probe may comprise a probe head and a cable. The probe head may include a light output configured to emit light into a head of the fetus and an acoustic transducer configured to detect acoustic pressure generated in response to the emitted light. The cable may extend out of the probe head to a monitor.

The probe head may be adapted to be held between two finger tips of a user. The probe head may be cylindrical. The light output may comprise a tip or output extending out from a housing of the probe head, such as from a center of the probe head. For example, the tip or output may comprise a protrusion of the optical fiber coupled to the light source. The light output may comprise an optical waveguide comprising a continuous rounded groove encircling a center of the probe head. The probe head may comprise a housing defining an interior space where the acoustic transducer is positioned and through which the light output passes. The light output may comprise one or more optical fibers. The acoustic transducer may comprise a piezoelectric transducer. The probe head may further comprise an amplifier for the acoustic transducer. The probe head may further comprise an electromagnetic shield that shields the acoustic sensor and amplifier from electromagnetic interference. The probe head may further comprise an acoustic attenuator configured to absorb undesired ringing in the probe head. The light output may be configured to channel light generated by a light source in the monitor.

The probe head may be configured to emit light having an energy of 10 to 1 mJ. The light emitted by the light output may have wavelengths in range of two or more of 685-715 nm, 715-745 nm, 745-775 nm, 790-820 nm, or 845-875 nm, such as two or more of 700 nm, 730 nm, 760 nm, 805 nm, or 860 nm, for example.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the present disclosure are set forth with particularity in the appended claims. A better understanding of the features and advantages of the present disclosure will be obtained by reference to the following detailed description that sets forth illustrative embodiments, in which the principles of the invention are utilized, and the accompanying drawings. Matching reference numerals designate corresponding parts throughout the figures, which are not necessarily drawn to scale.

DETAILED DESCRIPTION

Figure 1:
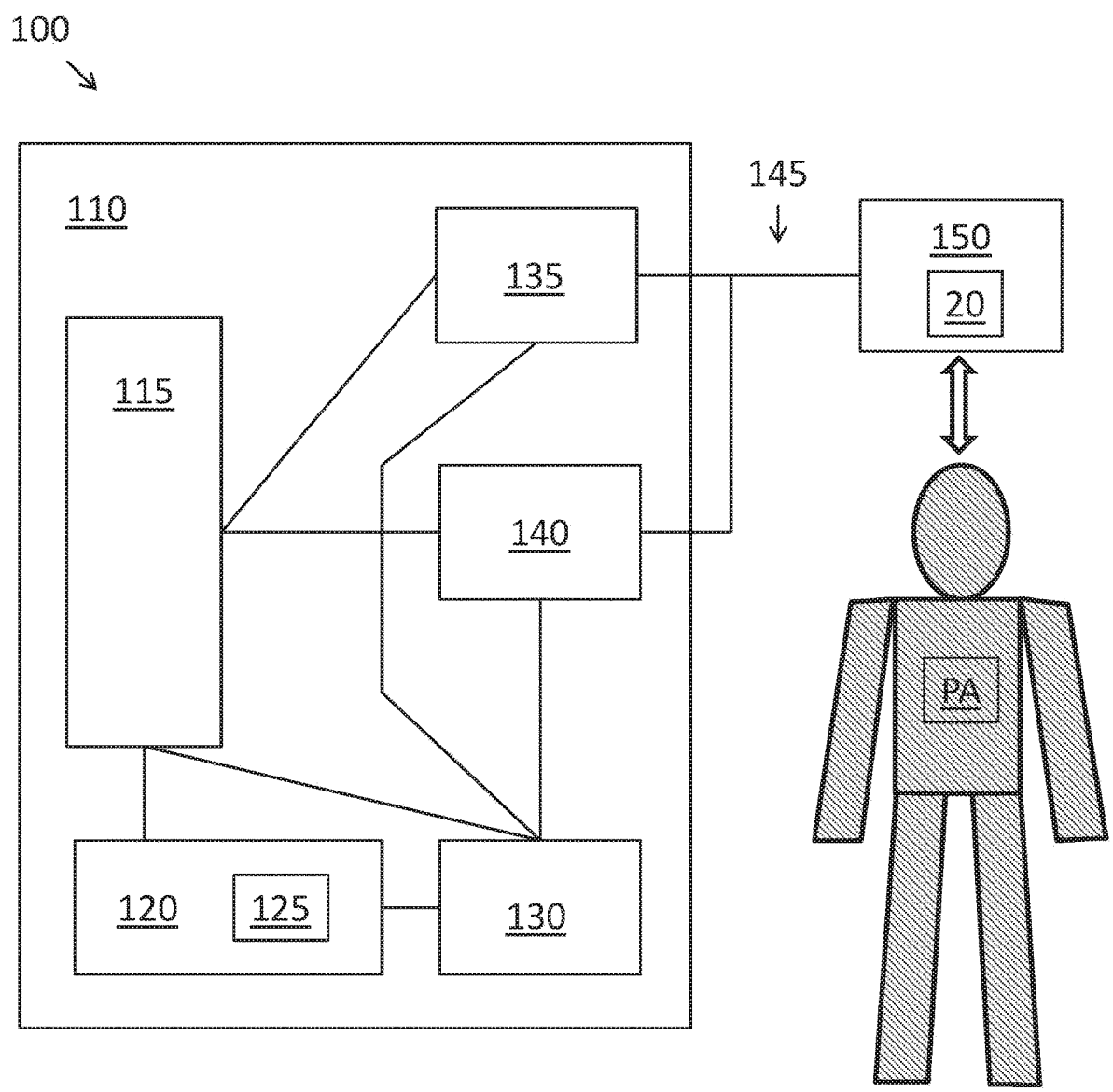
FIG. 1 shows a schematic diagram of a system for optoacoustic diagnosis of one or more physiological parameters, according to many embodiments.

As described above, it would be desirable to have a direct way of measuring fetal cerebral oxygenation, such as cerebral venous blood oxygenation saturation. Disclosed herein are systems and methods that are well suited for this purpose. In many embodiments, a system for measuring fetal cerebral oxygenation comprises a fetal cerebral oxygenation probe that can be applied to the fetus' head during labor. The probe can be an optoacoustic probe that is configured to emit light through the skull and brain tissue to the superior sagittal sinus (SSS) and receive back acoustic waves that are induced by the irradiation of the SSS. A determination of the blood oxygen saturation can then be made from the acoustic waves. In some embodiments, the probe is sized and configured to fit between the fingers of an obstetrician to facilitate application to the fetus' head and comprises a wave guide that emits the light and an acoustic sensor that detects the acoustic signal emitted from the SSS.

In the following disclosure, various specific embodiments are described. It is to be understood that those embodiments are example implementations of the disclosed inventions and that alternative embodiments are possible. All such embodiments are intended to fall within the scope of this disclosure.

Disclosed herein are systems and methods for monitoring cerebral oxygenation that can be used to perform accurate, noninvasive measurement of cerebral venous blood oxygen saturation in fetuses during late-stage labor through the open anterior fontanelle or through the thin cranial bones. Cerebral venous oxygen saturation provides in a single number an assessment of the ability of cerebral blood flow and cerebral blood oxygen content to meet cerebral oxygen requirements. As described below, the systems and methods enable optoacoustic measurement in the superior sagittal sinus (SSS). Such a measurement technique provides high contrast and high resolution that enables direct probing of blood vessels. Because cerebral venous desaturation provides direct evidence that cerebral oxygen availability is insufficient to satisfy cerebral oxygen requirements, decreasing SSS oxygenation ($SSS(SO_2)$) can provide an early warning of cerebral hypoxia. Therefore, this technique can be used to directly detect fetal asphyxia more rapidly than fetal heart rate (FHR) monitoring, thereby reducing the risk of cerebral palsy. This technique is also more specific than FHR monitoring, thereby reducing false-positive incidents of fetal distress and encouraging fewer defensive cesarean sections.

In contrast to previously studied techniques for assessing fetal viability during late-stage labor, optoacoustic monitoring of fetal $SSS(SO_2)$ during labor offers major advantages. In virtually all fetuses, the anterior fontanelle is palpable by vaginal examination once the maternal cervix has dilated to greater than 5 cm and virtually all fetal distress (detected by FHR monitoring only) occurs after that time. In infants, unlike adults, the sagittal sinus is directly below the scalp either without intervening skull or with thin overlying cranial bones, so relatively low-intensity light penetrates well. Because the generated ultrasound signal returns in a straight line from the SSS, the actual saturation of hemoglobin in the SSS can be accurately determined. While systems and methods for venous blood oxygenation detection are described, these systems and methods are equally applicable to detect arterial or other blood oxygenation.

FIG. 1 shows a schematic diagram of a system 100 for optoacoustically measuring physiological parameters such as blood oxygenation, for example, fetal cerebral oxygenation (e.g., fetal $SSS(SO_2)$) during labor or cerebral oxygenation generally such as for a patient with traumatic brain injury. The system 100 may comprise a console 110 and a patient interface 150 operatively coupled with a wire or cable connection 145. The console 110 may comprise a console comprising one or more subsystems or components configured to provide measurement of fetal cerebral oxygenation in a patient PA via the patient interface 150. The console 110 may comprise a computer board or processor 115, a user interface 120, a power supply subsystem 130, a laser emitter or diode subsystem 135, and an acoustic sensor subsystem 140. The processor 115 may be in communication with the one or more subsystems or components of the console 110, so as to control and monitor the operation of the subsystems. For example, the processor may comprise one or more universal serial bus (USB) ports or other types of data transfer ports configured to connect to the one or more subsystems. The processor 115 may further comprise an audio port to output alarms and message(s) through a speaker. The power supply subsystem 130 may be configured to provide power to one or more components of the system 110, such as the processor, user interface, laser diode subsystem, and acoustic sensor subsystem. The power supply subsystem 130 may be configured to connect to an external AC or DC power source and may comprise a battery to provide back-up power in case of loss of external power.

A user of the system 100, such as medical personnel trained to operate the system, can interact with the system via the user interface 120. The user interface 120 may, for example, comprise a display 125 such as a backlit LCD with a touch screen configured to receive one or more inputs from the user. The user interface 120 may further comprise hardware controls for controlling the operation of the system, such as on/off keys and a stop switch configured to put the system in a "safe" mode, wherein all laser diodes are turned off. The user interface 120 may also comprise an input for data such as patient identification, time, temperature, etc. The processor 115 can receive user input via the user interface 120, and transmit instructions based on the user input to one or more subsystems, such as the laser diode subsystem 135, acoustic sensor subsystem 140, and/or power supply subsystem 130. Based on instructions received from the processor 115, the laser diode subsystem 135 may generate and emit light pulses which may be directed to a target tissue of the patient PA through the patient interface 150. The light pulses can be conducted through the cable connection 145, such as a fiber optic cable and/or a multi-wire shielded cable, to the patient interface 150. For example, the light pulses can be transmitted to an optical fiber module of the patient interface 150 that is in contact with the target tissue, such as the superior sagittal sinus (SSS). The light pulses can pass through the tissue and bone to the venous blood, wherein absorption of the light pulses can result in the generation of acoustic pressure. The patient interface 150 can detect the acoustic pressure from the target tissue and transmit the acoustic signals back to the console 110, for example via the cable connection 145 to the acoustic sensor subsystem 140. The patient interface 150 can comprise, for example, a high speed digitizer configured to detect and digitize the acoustic pressure. The acoustic sensor subsystem 140 can receive and/or at least partially process the measured acoustic pressure signals then digitize the signals, and transmit the signals to the processor 115 for further processing and analysis. The processor 115 can, for example, compute the venous oxygen saturation from the measured acoustic pressure, and transmit results of the measurement to the user interface 120 to be displayed to the user via the display 125. The display 125 may be configured to display oxygen saturation readings (e.g., venous oxygen saturation readings) or other physiological parameters continuously, with updates once per minute, for example. In some embodiments, the system 100 may further comprise a communications subsystem to communicate with other electronic or computerized healthcare management systems. For example, the physiological parameter data measured may be stored and archived (to generate electronic medical records) and analyzed with another computerized system in communication with the system 100.

The system 100 may be configured to have a compact size to accommodate limited spaces available in transport vehicles, forward aid stations, or intensive care units. For example, the console 110 may be desktop-sized. Components of the system 100 may be ergonomically designed so as to allow easy operation for medical personnel who may be generally unfamiliar with optoacoustic measurements. The display 125 of the system 100 can provide user guidance for use of the system 100, as well as display the status of various alarms of the system 100, in order to help users understand causes of the alarms and take appropriate remedial actions. The system 100 may be configured to allow up to about 24 hours of continuous monitoring without changing locations. A power loss alarm may be implemented with the system 100, in order to alert the user of signal loss or cable disconnection during monitoring. The system 100 may further be configured to have a user-selectable transport mode that can support battery-operated use of the system 100 for up to about one hour. In the transport mode, the system 100 may be configured to operate with low power (e.g., lower power than in the operational mode), and the power loss alarm may be disabled. The system 100 may be further configured to allow users to input patient identification data, access patient medical records, and download the measurement data collected during the monitoring process for archival and evaluation purposes, for example through the communications subsystem described above.

The system 100 may be configured to monitor various physiological parameters. In many embodiments, oxygen saturation is measured. For example, venous oxygen saturation in the range from about 20% to about 100% (calculated as oxyhemoglobin÷total hemoglobin concentration [THb], as described further herein) may be measured. The system 100 may have an accuracy of about +/−3% over the saturation range from about 40% to about 90%, for example.

The acoustic sensor subsystem 140 may receive acoustic signals from the patient interface 150. The acoustic sensor subsystem 140 may comprise a one or more signal amplifiers configured to provide a gain for the received signals. The gain may be, for example, about 40 dB of gain at 500 kHz and may have, for example a −3 dB bandwidth of 50 kHz to 3.5 Mhz. The acoustic sensor subsystem 140 may comprise a high speed digitizer that may sample the amplified acoustic signal from the amplifier. This sampling may be performed at a minimum rate 20 MHz, for example. The digitizer may receive a trigger signal from the laser diode subsystem 135 and store samples, such as a 100, 200, 300, 400, 500, 600, 700, 800, 900, or 1000 samples, of the acoustic signal. The digitizer may transfer the block of samples to the processor 115 for waveform averaging. Often, the acoustic signals generated by the target tissue is low level and averaging readings over hundreds of repetitive cycles can extract the waveform out of background noise.

The patient interface 150 may comprise an optoacoustic sensor assembly or sensor module, such as the cerebral oxygenation probe 20 as described in further detail herein. An optoacoustic sensor assembly can comprise a light output configured to emit light pulses directed at the target tissue, and an acoustic transducer configured to measure the acoustic pressure generated in response to the light pulses. The light output may output light from a light source. The light source may comprise, for example, a light emitting diode (LED) array or a high power pulsed laser diode array configured to generate high intensity light pulses at one or more wavelengths. The light output can be connected to the console 110 via a fiber optic cable, for example. The light source may comprise the laser diode subsystem 135 of the console 110. The acoustic transducer can comprise, for example, a piezoelectric sensor, connected to the console via a multiwire shielded cable. The cables 145 connecting the patient interface 150 and the console 110 may comprise connectors to removably couple the cables to the console. The light source and the acoustic transducer may be supported with a probe that can be placed over a portion of the patient's head, such as the surface of the scalp over the SSS. The probe 20 may be held in place with a strap system, which may comprise a disposable, single-use mounting strap in order to reduce or eliminate the need for cleaning and disinfection between uses.

Figure 2:
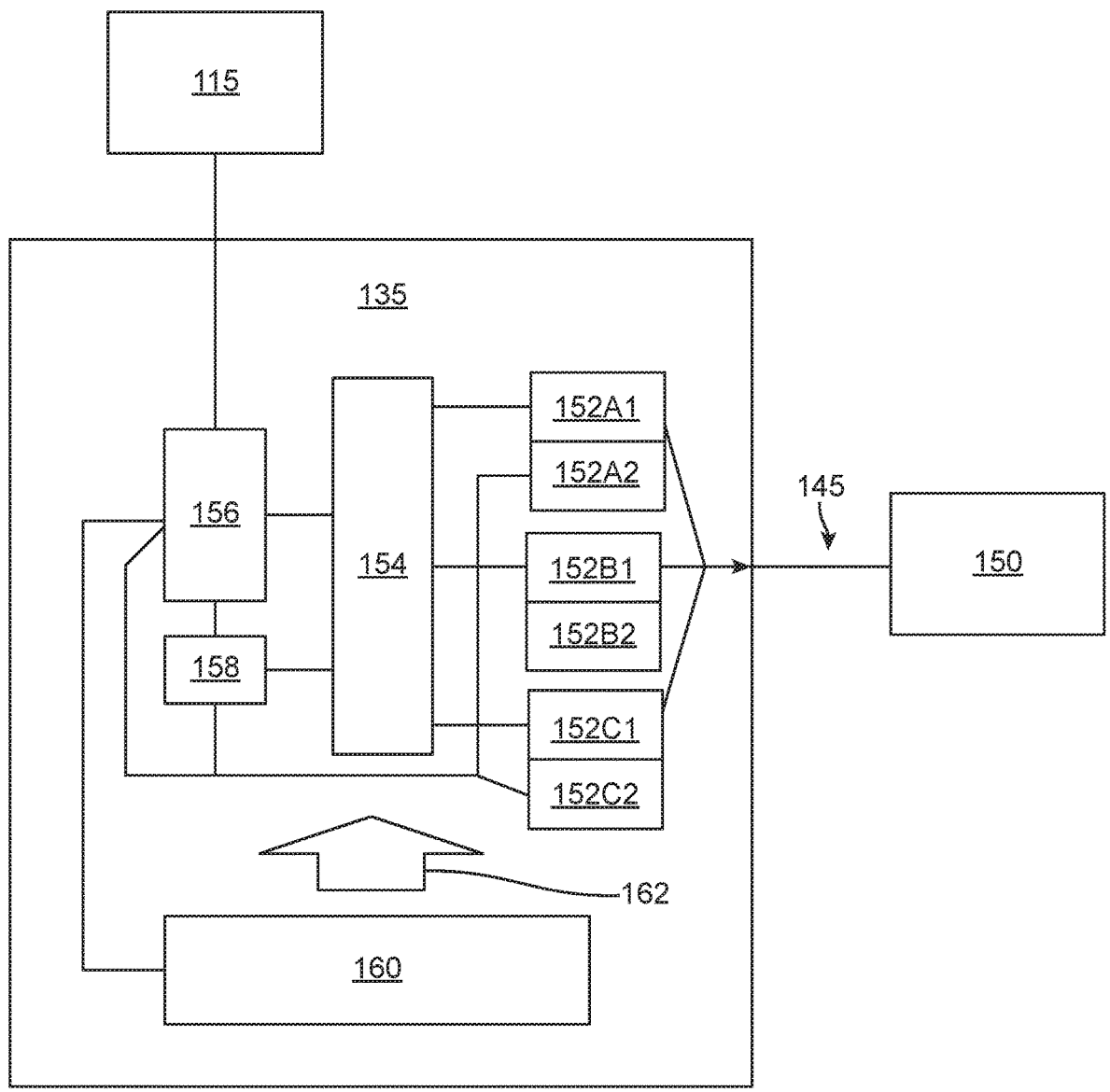
FIG. 2 shows a schematic diagram of an exemplary laser diode subsystem of the system of FIG. 1.

FIG. 2 shows a schematic diagram of the laser diode subsystem 135 of the system 100 of FIG. 1. The laser diode subsystem 135 may comprise a laser diode array comprising, for example, a first laser emitter or diode 152A1, a second laser emitter or diode 152B1, and a third laser emitter or diode 152C1. The laser diode subsystem 135 may comprise a laser control processor 156 in communication with the processor 115 of the console 110 of the system. The laser control processor 156 can receive instructions from the console processor 115 based on one or more user inputs provided to the console 110. For example, the processor 115 can set and monitor operational parameters, and start and stop measurement cycles by the laser diode subsystem 135. The laser diode subsystem 135 may further comprise a laser supervisor processor 158, in communication with the laser control processor. The laser supervisor processor 158 may monitor the operation of the laser diodes 152A1, 152B1, and/or 152C1 to ensure that the temperature of the diodes 152A1, 152B1, and/or 152C1 is substantially constant or within an acceptable range to maintain wavelength accuracy. For example, an acceptable operational temperature range may be from 10° C. to 40° C. Together, the laser control processor 156 and the laser supervisor processor 158 can control and monitor the operation of one or more laser drivers 154. The laser controllers 154 can be configured to receive instructions from the laser control processor 156 and the laser supervisor processor 158, and in response to the received instructions, control operation of the laser emitter or diodes 158A, 152B1, and/or 152C1 coupled to the laser controllers 154. The laser controllers 154 can further be configured to control operation of one or more laser emitter coolers, such as coolers 152A2, 152B2, and/or 152C2, coupled to and configured to cool the corresponding laser emitters 152A1, 152B1, and/or 152C1, respectively. The laser controllers 154 may comprise laser drivers for the laser diodes 152A1, 152B1, and 152C1 and their respective coolers 152A2, 152B2, and 152C2. For example, the laser emitter coolers may comprise thermoelectric coolers (TEC) and/or two temperature sensors (primary and secondary) mounted on the back of each laser diode 152A1, 152B1, and/or 152C1. The temperature sensors can be configured to measure the temperature of the laser diodes 152A1, 152B1, and/or 152C1, and the TECs can be configured to control the temperature of the laser diodes 152A1, 152B1, and/or 152C1 to keep them in an optimal operational temperature range, such as by adding or removing heat depending on the temperature measured and the temperature range desired. For example, the wavelengths of the laser diodes 152A1, 152B1, and 152C1 may have a dependency of about 0.3 nm/deg C. The laser drivers may be configured to generate high amperage, short duration current pulses to drive the laser diodes 152A1, 152B1, and 152C1. The light pulses generated by the laser emitters 152A1, 152B1, and/or 152C1 can be conducted through the cable connection 145 to a patient interface 150, which may comprise an optoacoustic sensor assembly or probe as described herein.

The laser diode subsystem 135 can further comprise a cooling fan 160, configured to provide an air stream shown by the arrow 162, directed towards to the components of the laser diode subsystem 135. Such a cooling fan 160 can help control the temperature of the components, which may be disposed in a closed laser cavity to as to prevent dust contamination of the optical components. The cooling fan 160 may further comprise a second fan configured to circulate outside air over the control electronics. The laser cavity may be surrounded by a laser diode subsystem enclosure, constructed from metal plates. The enclosure of the laser diode subsystem 135 can be securely mounted to the enclosure for the console 110, for example via mechanical fasteners.

At start-up, the laser diode subsystem 135 may have a temperature stabilization time for the laser diodes 152A1, 152B1, and/or 152C1. The temperature stabilization status can be displayed on the display 125 of the console 110. During operation of the laser diodes 152A1, 152B1, and/or 152C1, the operational parameters of the laser diodes 152A1, 152B1, and/or 152C1, including the temperature measurements generated by the laser emitter coolers 152A2, 152B2 and/or 152C2, can be transmitted back to the laser control processor 156 and/or the laser supervisor processor 158, for feedback control of laser diode operation. For example, in embodiments wherein the laser emitter coolers comprise a TEC and temperature sensors coupled to each laser diode, the laser control processor 156 can comprise instructions to drive current through the TEC to control the measured temperature from the temperature sensors.

The laser emitters 152A1, 152B1, and/or 152C1 of the laser diode subsystem 135 may comprise pulsed laser diodes having nominal center wavelengths of about 760 nm, 800 nm, and 860 nm, respectively, for example. Other wavelengths such as 700 nm, 730 nm, 850 nm, 905 nm, 970 nm, 975 nm, 1064 nm, 1100 nm, 1200 nm, 1230 nm, and 1450 nm, to name a few, are also contemplated. The wavelengths may be chosen to correspond with the peak acoustic response of parameters of interest such as water, fat, hemoglobin, oxyhemoglobin, deoxyhemoglobin, carboxyhemoglobin, reduced hemoglobin, methemoglobin, lactate, myoglobin, cholesterol, body pigments, exogenous dyes such as indocyanine green (ICG), to name a few. While the determination of blood oxygenation is discussed herein, the interrogation of other physiological parameters and concentrations is also contemplated. The concurrent determination of two or more physiological parameters or concentrations is described in U.S. Publication No. 2008/0255433 A1, which is incorporated herein by reference.

The nominal center wavelengths may have a stability of about +/−1 nm, 0.9 nm, 0.8 nm, 0.7 nm, 0.6 nm, 0.5 nm, 0.4 nm, 0.3 nm, 0.2 nm, or 0.1 nm over the operational temperature range. The spectral width (full width half maximum) of the light output of each laser diode may be about 25 nm, 20 nm, 15 nm, 10 nm, 5 nm, or 1 nm nominally, as measured at 50% of peak output. Each laser diode 152A1, 152B1, and/or 152C1 may comprise a driver configured to deliver about 3.3 kW peak power (nominal) with a pulse width of about 150 ns (measured at 50% of amplitude) and a repetition rate of about 10 to about 2000 Hz, or about 0.5% of setting. Each light pulse can be configured to deliver about 0.5 mJ of energy (3300 W×150 ns), nominally. The output of a plurality of laser diodes 152A1, 152B1, and/or 152C1 can be combined together into a single fiber. For each light pulse, the laser diode subsystem 135 may be configured to output a trigger signal to a digitizer coupled to the laser diode subsystem 135, such that the digitizer may start the sampling sequence.

While an array of three laser diodes is described, other configurations are also contemplated. For example, the array may have two laser diodes or four or more laser diodes. Alternatively or in combination to using an array of laser diodes to produce light output at different wavelengths, the laser subsystem 135 may comprise an optical parametric oscillator (OPO) to rapidly switch a laser output between multiple wavelengths.

Figure 3:
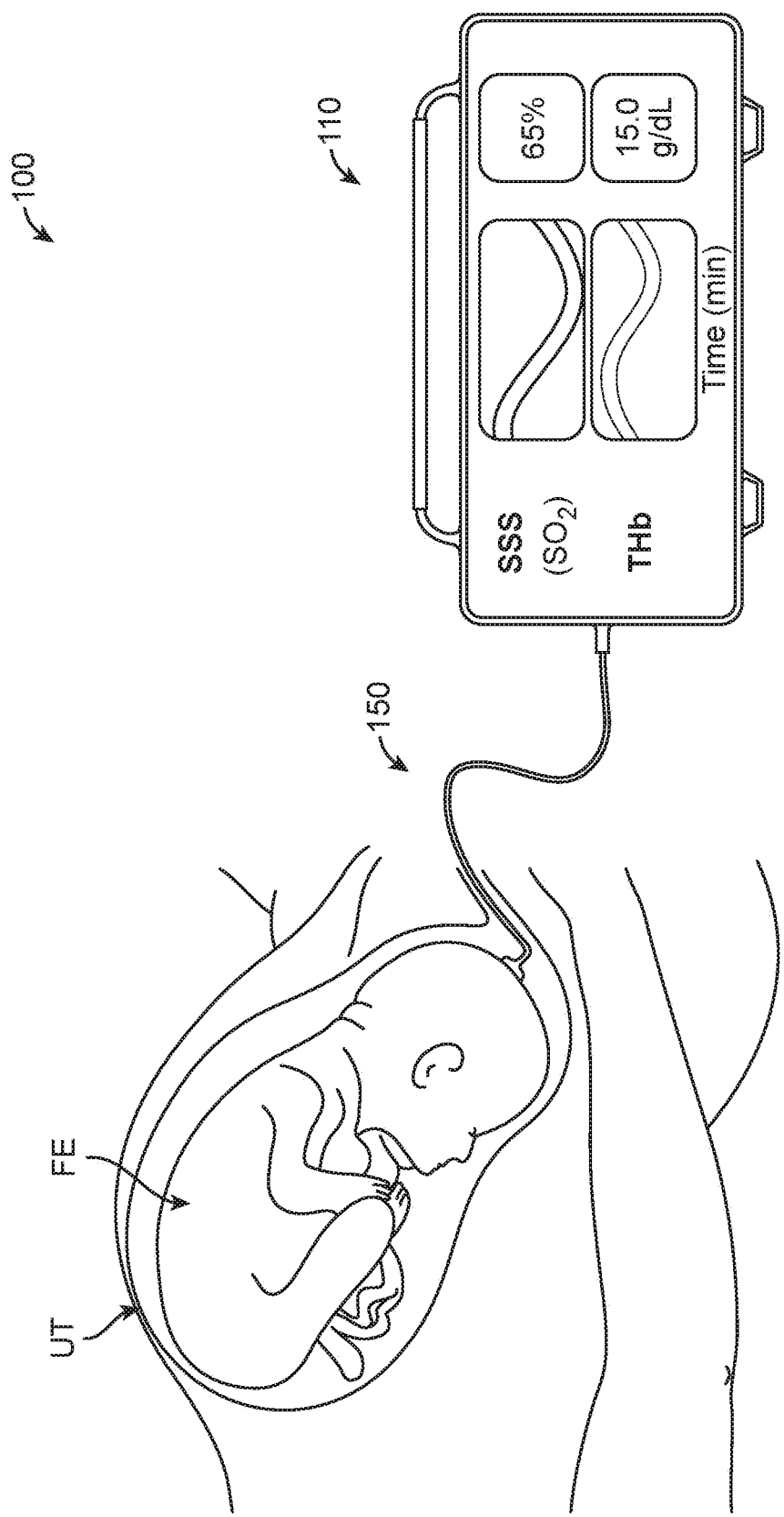
FIG. 3 is a schematic view of an embodiment of a system for measuring fetal cerebral oxygenation, according to many embodiments.

FIG. 3 illustrates the system 100 in use to measure cerebral oxygenation (such as SSS(SO$_2$)) of a fetus FE present in the uterus UT during labor. As shown in FIG. 3 and described above and herein, the system 100 generally comprises an optoacoustic monitor or console 110 and the patient interface or cerebral oxygenation probe 150 that is connected to the monitor. The monitor or console 110 may comprises a light source such as the photodiode subsystem 135 that generates light, such as near infrared (NIR) laser light that can, as indicated in FIG. 3, be emitted from the tip of the probe 150 and into a fetus' head. The absorption of the light's energy in a medium can be followed by thermal expansion of the irradiated medium, in this case the blood in the SSS, which induces mechanical stress that propagates in the form of acoustic (e.g., ultrasonic) pressure waves. These waves can travel through the brain tissue with minimal scattering and can be detected by an acoustic sensor within the probe that converts the waves into electrical signals that can be provided to the monitor or console 110 and/or to a computer for processing.

In some embodiments, the emitted light is within the low end of the NIR spectral range, such as approximately 600 to 1300 nm, for example 760 nm, 800 nm, and 860 nm as discussed above and herein. Such a wavelength range can result in deep penetration of the NIR radiation, which is sufficient for optoacoustic monitoring of hemoglobin saturation. The amount of laser energy applied for monitoring may be small and cannot induce any thermal or mechanical damage to a patient's skin or a patient's or operator's ocular tissues because laser fluence levels are well below the maximum permissible exposures (MPE) for ocular tissues. In some embodiments, the laser energy is delivered at a power of approximately 1 µJ to 1mJ.

Oxyhemoglobin and deoxyhemoglobin have high absorption coefficients in the visible and NIR spectral range. Therefore, both the amplitude and spatial distribution of the generated optoacoustic pressure induced in blood are generally dependent on total hemoglobin concentration [THb] and hemoglobin saturation (calculated as oxyhemoglobin [THb]). The high resolution of the disclosed measurement technique enables direct measurement of [THb] and saturation in large blood vessels. In some embodiments, saturation can be assessed using an optical parametric oscillator (OPO) pumped by Nd-YAG laser to generate four important wavelengths: 800 or 805 nm (isosbestic point where oxy- and deoxyhemoglobin have equal absorption) and 700, 730, and 760 nm, which are wavelengths at which oxy- and deoxyhemoglobin have strong differences in absorption. In some embodiments, the concentration of different molecules may be of interest such that other wavelengths are chosen. For example, one of the photodiodes 152A1, 152B1, and/or 152C1 may be configured to output a light signal at 860 nm, the wavelength at which an exogenous dye such as indocyanine green (ICG) shows very low acoustic response, while at about 900 nm, it has a peak acoustic response. This contrast may provide high accuracy of ICG monitoring.

The acoustic signal generally returns in a straight line from the target. Laser optoacoustic imaging techniques combine the merits of optical tomography (high optical contrast) and ultrasound imaging (minimal scattering of acoustic waves) to yield a noninvasive diagnostic modality with high contrast, sensitivity, and resolution. The high resolution, sensitivity, and contrast of optoacoustic techniques provide monitoring of [THb], oxygenated and deoxygenated hemoglobin with excellent accuracy, specificity and sensitivity. Transmission of ultrasound signals in a straight line differentiates optoacoustic measurements from pure optical techniques in which both incident and returning optical signals are scattered by passage through tissue. Optoacoustic imaging can visualize structures in optically turbid and opaque tissues at depths as great as several centimeters with a spatial resolution <0.5 mm and can reconstruct optoacoustic images. In summary, the merits of optoacoustic monitoring include, but are not limited to: (1) noninvasiveness, (2) accurate, quantitative measurements, (3) continuous, real-time monitoring, (4) high spatial resolution, and (5) compact dimensions.

Figure 4:
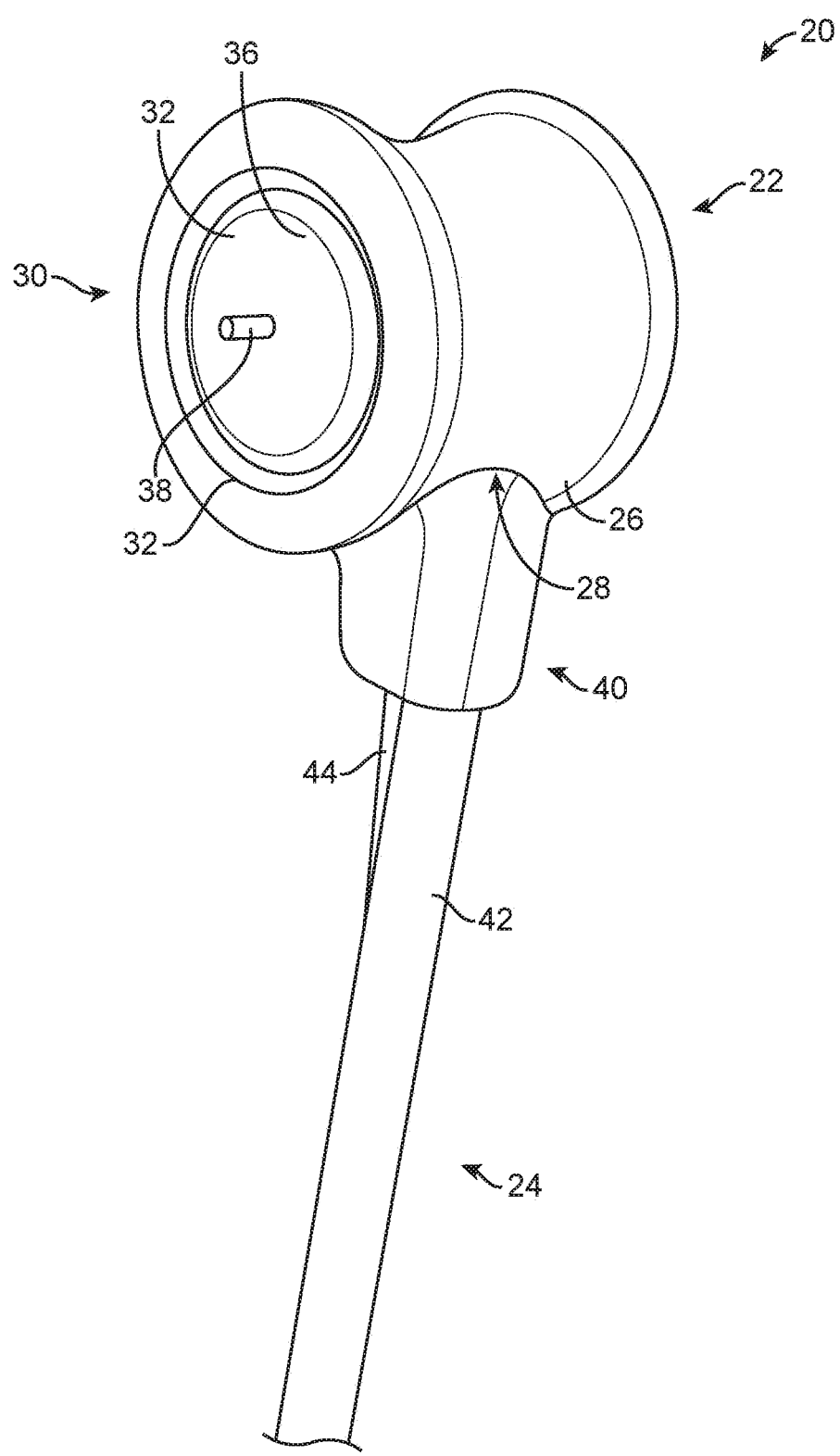
FIG. 4 is a perspective view of an embodiment of a fetal cerebral oxygenation probe that can be used in the system of FIG. 3, according to many embodiments.
Figure 5:
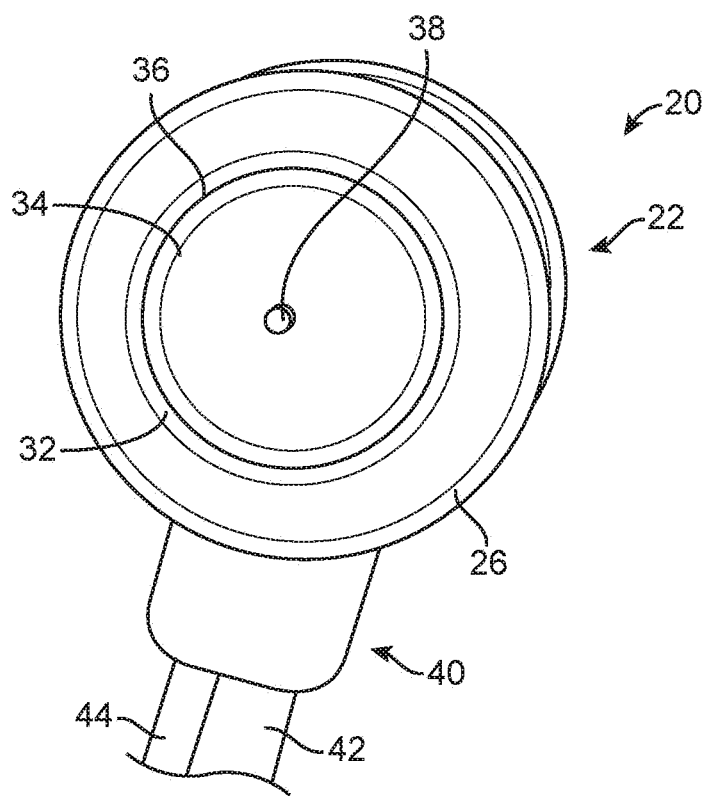
FIG. 5 is a front view of the fetal cerebral oxygenation probe of FIG. 4.
Figure 6:
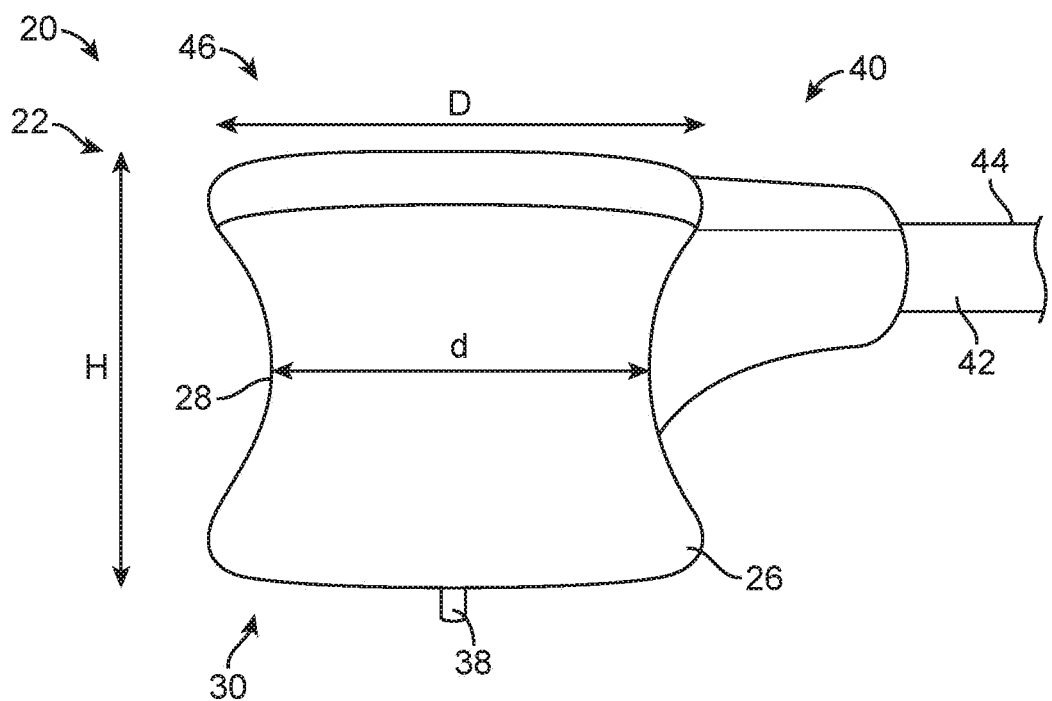
FIG. 6 is a side view of the fetal cerebral oxygenation probe of FIG. 4.

FIGS. 4-6 illustrate an example a cerebral oxygenation probe 20 that can be used in the system 10 shown in FIG. 3. The patient interface 150 may comprise the probe 20. As the probe 20 may be designed to emit light and detect acoustic waves, the probe can be referred to as an optoacoustic probe. Generally speaking, the probe 20 comprises a head 22 from which may extend one or more cables 24 that connect the probe 20 to the remainder of the system 100.

The head 22 can be made of a biocompatible polymeric material such as polyamide (e.g., PA 2200), polycarbonate (e.g., PC-ISO), or acrylonitrile butadiene styrene (e.g., ABS-M30) and can comprise one or more pieces. In cases in which the head 22 comprises more than one piece, the pieces may be sealed together so as to prevent the ingress of air or fluid into the interior of the head. As is apparent from FIGS. 4-6, the head 22 can comprises a generally cylindrical housing 26. The medial portion of the housing 26 (along its longitudinal axis) can be narrower than the ends of the housing. More particularly, the housing 26 may gradually narrow from each housing end so that the center of the housing is its narrowest point. Because of this a configuration, the housing 26 may have a rounded hourglass shape that can be seen most clearly in FIG. 6. This shape can form a continuous rounded groove 28 that encircles the center of the housing 26. In some embodiments, this groove 28 has a radius of curvature of approximately 5 to 50 mm. As described below, this groove 28 can facilitate gripping of the head 22 during an oxygenation measurement procedure. Although the dimensions of the housing 26 can be varied to suit the application and/or the user, in some embodiments, the housing is approximately 5 to 30 mm in height (H), the ends of the housing are approximately 8 to 20 mm in diameter (D), and the center of the housing is approximately 3 to 15 mm in diameter (d) (see FIG. 6). As is also apparent in FIG. 6, the edges of the ends of the housing 26 can be rounded. The head 22 can comprise a flexible or soft material, or a rigid material having smooth edges, the material preferably providing electrical isolation of the electrical components housed within the probe 20.

As indicated most clearly in FIGS. 4 and 5, the front end 30 of the housing 26 is the working end of the probe, which is configured to interface with the head of the fetus. At this end of the probe 20, the housing 26 may comprise a circular opening 32 that provides access to the housing interior.

Visible through this opening 30 may be an internal electromagnetic shield 34 that is positioned behind a cover 36 that seals the opening 32. Extending from the center of the cover 36 along a direction parallel to the longitudinal axis of the housing 26 may be the tip of an optical waveguide 38. The nature and function of these components are described below in relation to the cross-sectional view of FIG. 7.

With further reference to FIGS. 4-6, extending from the housing 26 is a strain relief element 40 that provides strain relief for the cables 24 extending from the probe head 22. In some embodiments, the strain relief element 40 can be made of the same material as the housing 26 and may be unitarily formed therewith. As shown in FIGS. 4-6, the cables 24 may include an electrical cable 42 and an optical cable 44, which are used to transmit electrical and optical signals, respectively. It is noted, however, that these cables 42, 44 can be combined into a single cable, if desired. As indicated most clearly in FIG. 6, the strain relief element 40 can extend out from the rear end 46 of the housing 26 in a direction that is generally perpendicular to the longitudinal axis of the housing. As is apparent from comparison of FIGS. 5 and 6, the stain relief element 40 can have a width dimension (FIG. 5) that is greater than its height dimension (FIG. 6). The optical cable 44 may be flexible and small (e.g., diameter of about 1 mm), such that the cable can bend to fit in housing.

The housing 26 and the strain relief element 40 can be configured to allow the user to position the probe over the anterior fontanel of a fetus head positioned in various orientations, and over a range of depths within the birth canal. For example, the probe 20 may be dimensioned to fit between the fetus head and the cervix wall, or to sit on top of the fetus head in the cervical opening. The strain relief element may be configured to have a flexible or adjustable angle of exit for the cables, in order to allow the user to move the probe to the appropriate position for measurement.

Figure 7:
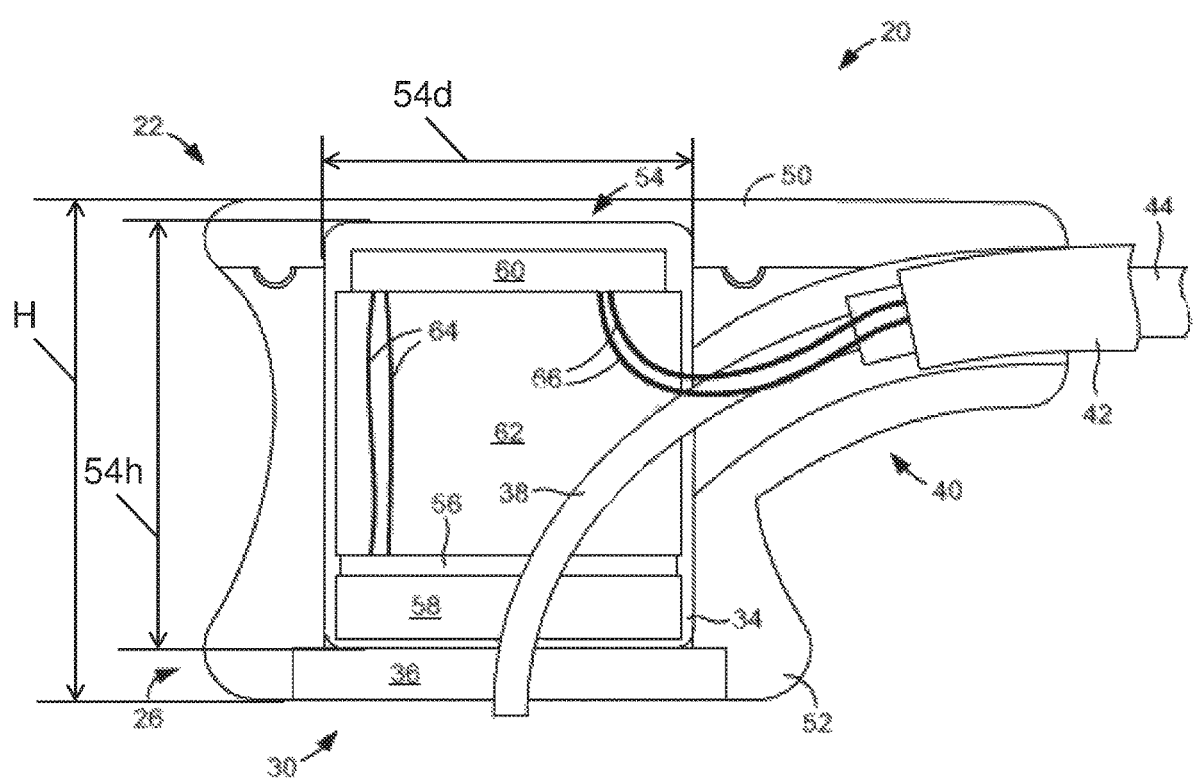
FIG. 7 is a cross-sectional side view of the fetal cerebral oxygenation probe of FIG. 4.

FIG. 7 illustrates an example construction for the optoacoustic probe 20 shown in FIGS. 4-6. As indicated in FIG. 7, the probe head 22 can be formed from two pieces of material that are coupled together to define the housing 26 and the strain relief 40. Alternatively, the probe head 22, including the housing 26 and the strain relief 40, may be formed from a single, integral piece of material. More particularly, the head 22 can comprise a top portion 50 and a bottom portion 52 that each defines part of the housing 26 and the strain relief 40 and that are attached to each other so as to seal a hollow interior space 54 in which internal components of the probe reside. As is indicated in FIG. 7, these components include the electromagnetic shield 34, cover 36, and optical waveguide 38 referenced above, as well as an acoustic sensor 56, a spacer element 58, a printed circuit board (PCB) 60, and an acoustic backing material 62. The purpose of each of these components is described below.

The electromagnetic shield 34 may be an element that surrounds the other internal components of the probe 20, including the acoustic sensor 56 and the PCB 60, and may shield them from electromagnetic interference. The shield 34 may be made of an electrically conductive material, such as copper foil, and can act as a shield from electromagnetic noise that would otherwise interfere with the proper operation of the probe 20.

The cover 36 can insulate the electromagnetic shield 34 and seals the front end 30 of the housing 26 to prevent air or liquid from passing through its opening 32. In some embodiments, the cover 36 is made of a transparent polymeric material, such as poly(methyl methacrylate).

The optical waveguide 38 can be used to deliver pulsed NIR light to the tissues within the brain of the fetus so as to induce ultrasonic waves from the SSS that can be detected by the acoustic sensor 56. The optical waveguide 38 can comprise a single optical fiber or multiple optical fibers. In the latter case, the optical fibers can be bundled together, as with an optical fiber cable, or can be spatially separated from each other. In some embodiments, the optical waveguide 38 comprises a single optical fiber having a 10 to 1,500 μm core and an outer diameter of approximately 12 to 2,000 μm. Irrespective of the particular nature of the optical waveguide 38 that is used, the tip of the waveguide extends beyond the outer surface of the cover 36. This extension can facilitate placing the optical waveguide 38 in direct contact with the scalp in cases in which the fetus has a significant amount of hair. In some embodiments, the tip extends approximately 1 to 3 mm beyond the outer surface of the cover 36. For example, the optical waveguide may comprise a plurality of optical fibers having a diameter of about 1 mm, protruding from the housing to form a "brush" of fibers that can pass through the hair to contact the scalp, thereby reducing loss of light intensity due to absorption by the hair. The optical fibers may extend through the center of the bottom of the housing as shown in FIG. 7, and extend about 2 mm beyond the outer surface of the cover 36. The plurality of fibers may be spaced center-to-center in such a way that the fibers can be located over the SSS. The fibers are preferably configured to be comfortable for up to 24 hours of continuous contact with the target tissue.

As mentioned above, the acoustic sensor 56 can detect the ultrasonic waves that are generated by the SSS of the fetus. In some embodiments, the acoustic sensor 56 comprises a piezoelectric transducer that uses the piezoelectric effect to measure changes in pressure, acceleration, strain, or force and convert them into an electrical signal. The sensor 56 may be separated from the electromagnetic shield 34 by the spacer element 58, which can be made of a polymeric material, such as polyamide. In some embodiments, the spacer element 58 is approximately 0.005 to 5 mm thick.

The electrical signals generated by the acoustic sensor 56 are transmitted to the PCB 60 via one or more electrical wires 64. The PCB 60 comprises a preamplifier that amplifies the signals received from the sensor 56 before transmitting them to a monitor or computer of the system along further electrical wires 66. The preamplifier can be configured to provide about 40 dB of gain at about 500 kHz, having a bandwidth of about 3 dB in the range from about 40 kHz to about 10 MHz. The PCB may further comprise a digitizer configured to digitize the acoustic signal detected by the acoustic sensor 56. For example, the digitizer can be configured to sample the acoustic signal from the preamplifier at least at about 20 MHz, in response to a trigger signal from the laser diode subsystem connected to the probe, as described herein. The digitizer can, for example, store about 1000 samples of the acoustic signal, and transfer the block of samples to the processor of the console unit 100 connected to and controlling the operation of the optoacoustic probe, for waveform averaging of the samples.

The acoustic backing material 62 is positioned behind the acoustic sensor 56. It provides backing for the sensor 56 (for wideband detection of pressure waves) and absorbs the vibrations that travel through the sensor to prevent undesired ringing in the signal and separate part of the signal from ringing noise. In some embodiments, the attenuator 62 comprises a mass of epoxy.

The hollow interior space 54, within which the internal components of the probe reside, may be substantially cylindrical as shown in FIG. 7, with a diameter 54d in a range from about 8 to about 10 mm, and a height 54h of about 10 mm.

The probe 20 may be designed to reduce areas that cannot be easily cleaned and disinfected between uses, such as grooves or pockets of in the exterior surface of the housing. Alternatively or in combination, the probe 20 may comprise a disposable cover configured to be placed over the housing, in order to reduce the need for cleaning and disinfecting the probe between uses. The probe 20 is preferably configured such that its components can withstand soaking in a disinfecting solution for sterilization.

Figure 11A:
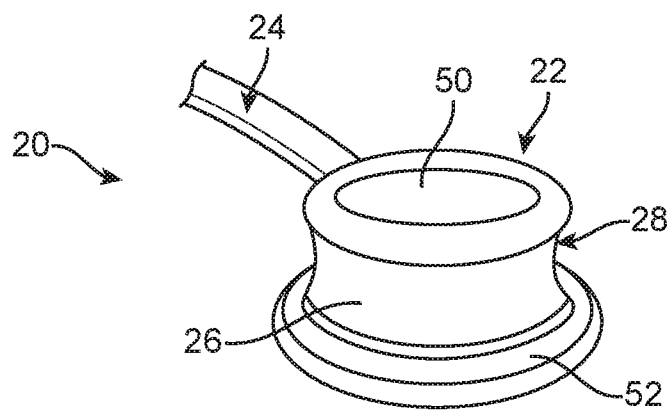
FIGS. 11A and 11B illustrate an exemplary configuration of an optoacoustic probe, according to many embodiments.
Figure 11B:
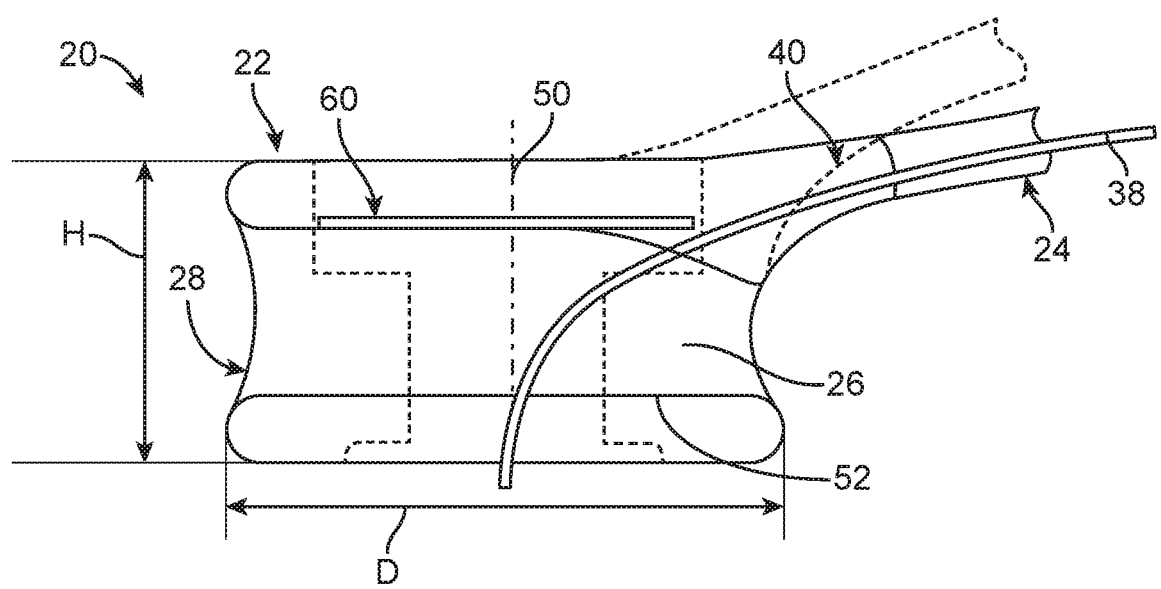

FIGS. 11A and 11B illustrate an exemplary configuration of an optoacoustic probe 20 as described herein. The probe 20 may comprise a head 22 extending from a cable bundle 24 connected to a console that controls operation of the probe, such as console 110 described in reference to FIGS. 1 and 2. The head 22 can comprise a housing 26, a top portion 50, and a bottom portion 52 comprising substantially the same shape. For example, the housing 26 can have a substantially cylindrical shape, for example with a diameter D in a range from about 30 mm to about 40 mm and a height H of about 18 mm. The top portion 50 and bottom portion 52 may be substantially circular with substantially the same diameter D, oriented substantially parallel to one another. The housing can comprise an annular groove 28 extending continuously about the side of the housing at the center portion of the housing. The groove 28 can form a concave side surface of the housing that facilitates gripping of the probe head 22 by the user while the user places the bottom portion 52 in contact with the target tissue for oxygenation measurement.

Figure 12A:
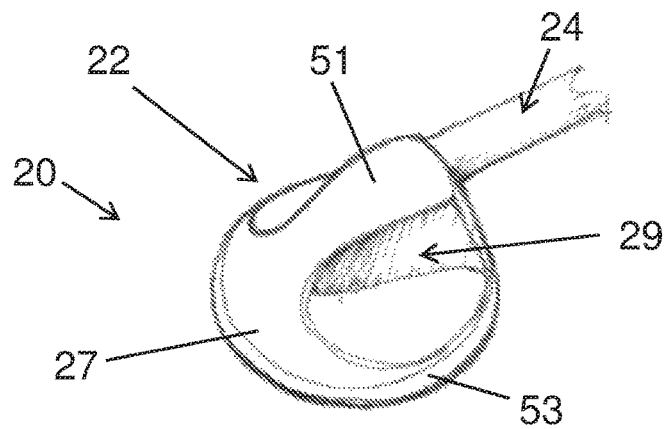
FIGS. 12A and 12B illustrate another exemplary configuration of an optoacoustic probe, according to many embodiments.
Figure 12B:
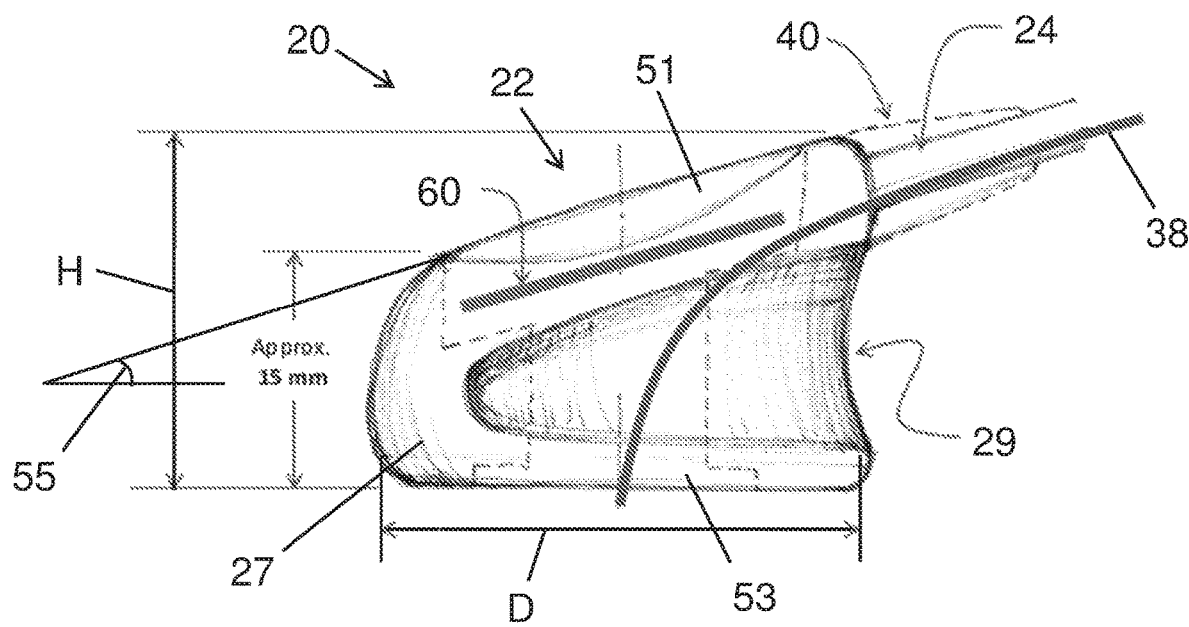

FIGS. 12A and 12B illustrate another exemplary configuration of an optoacoustic probe 20 as described herein. The probe 20 may comprise a head 22 extending from a cable bundle 24 connected to a console that controls operation of the probe, such as console 110 described in reference to FIGS. 1 and 2. The head 22 can comprise a housing 27 having a top portion 51 and a bottom portion 53 comprising different shapes. For example, the bottom portion 53 may comprise a substantially circular shape having a diameter D, while the top portion 51 may comprise an elongated shape extending over the diameter D of the bottom portion. The plane of the top portion 51 may be disposed at an angle 55 with respect to the plane of the bottom portion 53, such that a first end 51a of the top portion connects directly to the bottom portion 53. The maximum height H of the housing may be about 25 mm, and the diameter D of the bottom portion may be about 30 mm to about 40 mm. The housing may comprise a groove 29 extending continuously about a portion of the side of the housing. As shown in FIG. 12B, the groove 29 may have a taper that corresponds to the angle 55 between the top portion 51 and bottom portion 53 of the housing, such that the groove terminates at the point the first end 51a of the top portion connects with the bottom portion. The groove 29 may form concave rear and side surfaces of the housing that facilitate gripping of the probe head 22 by the user while the user places the bottom portion 53 in contact with the target tissue for oxygenation measurement. The strain relief element 40, coupled to the probe head 22 and configured to relieve strain placed on the cables 24, may have a streamlined or tapered shape as shown.

Figure 8:
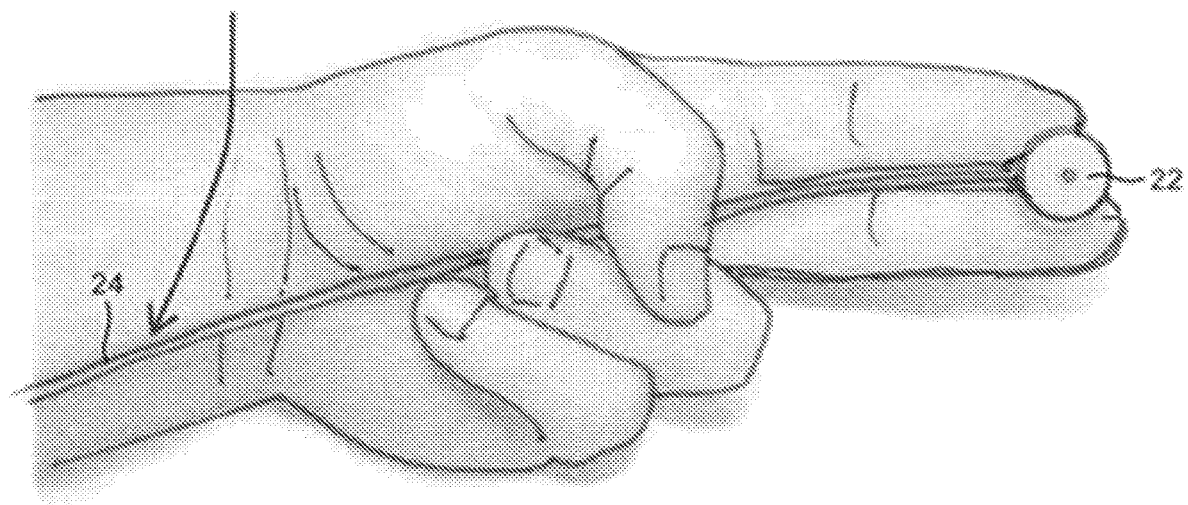
FIG. 8 is a schematic view illustrating a first example grip used to hold a fetal cerebral oxygenation probe during a fetal examination, according to many embodiments.
Figure 9:
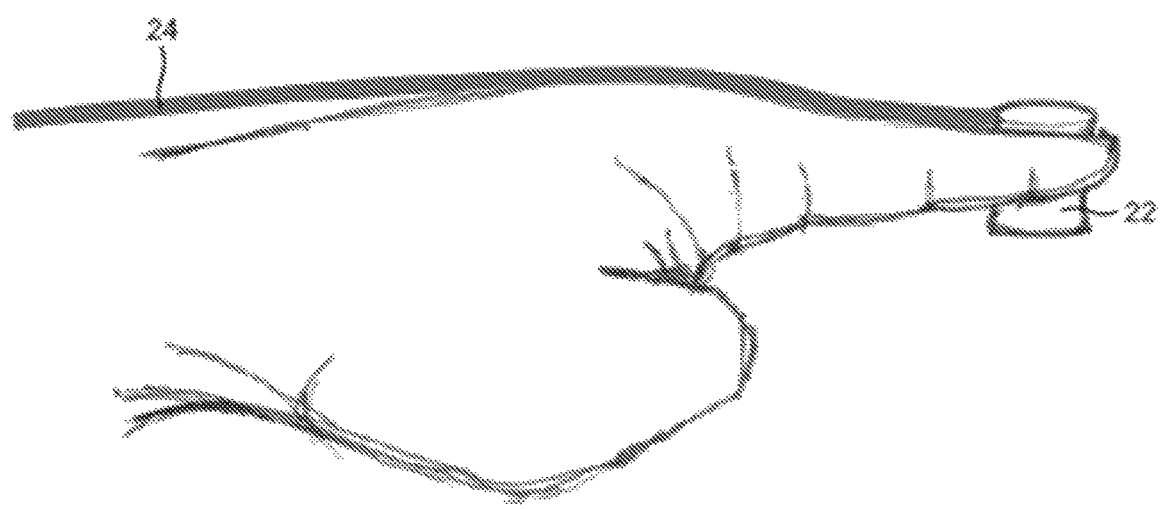
FIG. 9 is a schematic view illustrating a second example grip used to hold a fetal cerebral oxygenation probe during a fetal examination, according to many embodiments.

FIGS. 8 and 9 illustrate two examples of the manner in which the probe 20 can be grasped by an obstetrician during a fetal cerebral oxygenation measurement procedure. In both cases, the head 22 of the probe is pinched between the tips of the index and middle fingers. As shown in the figures, the groove 28 within the probe head housing 26 facilitates the pinch grip. The cable(s) 24 of the probe 20 can be run either along the inside of the hand, as indicated in FIG. 8, or along the outside of the hand, as indicated in FIG. 9. Once the desired grip and cable routing have been attained, the obstetrician can then insert his hand through the vagina and into the birth canal to place the front end of the probe head 22 in contact with the head of the fetus, as illustrated in FIG. 3. Measurements can then be obtained using the probe 20 and processed to determine cerebral oxygenation. Preferably, the probe head 22 is placed over the anterior fontanel of the head of the fetus, wherein the fetus is in any head down position (e.g., direct occiput anterior (OA), left occiput anterior (LOA), right occiput anterior (ROA), left occiput transverse (LOT), right occiput transverse (ROT), direct occiput posterior (OP), left occiput posterior (LOP), right occiput posterior (ROP)). In a typical scenario, the fetus's head may be recessed about 50 mm into the birth canal and the cervix may be dilated to about 4 to 5 cm. The insertion, positioning, and measurement with the optoacoustic probe can have a duration of about 30 to about 45 seconds, for example.

The probe 20 may be used with ultrasound gel, or may be used without ultrasound gel with the probe head in close contact with the fetal scalp. If used without ultrasound gel, the inherent moisture in the environment surrounding the probe head may provide adequate acoustic coupling.

Figure 13A:
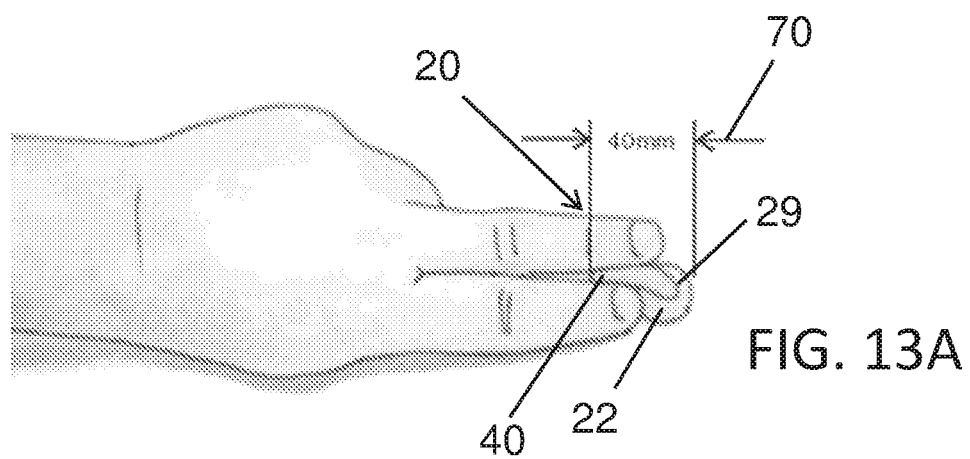
FIGS. 13A, 13B, and 13C illustrate a probe as grasped by a user during a fetal cerebral oxygenation measurement procedure, according to many embodiments.
Figure 13B:
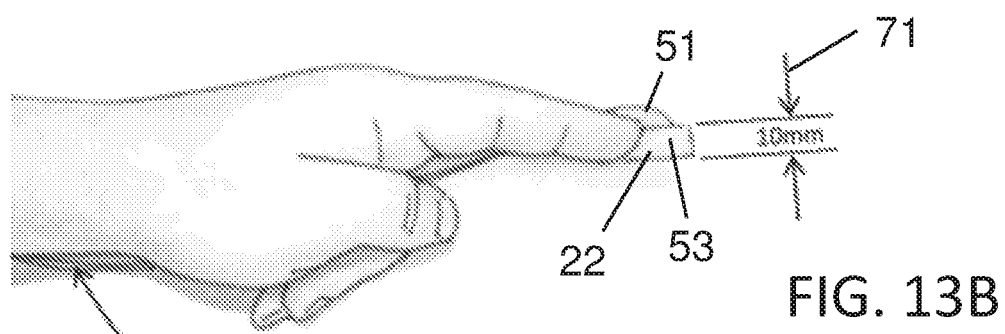
Figure 13C:
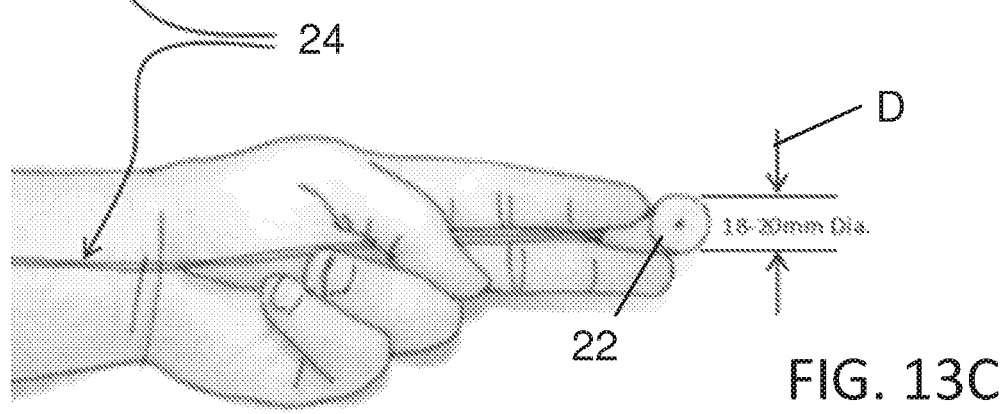

FIGS. 13A-13C illustrate an exemplary configuration of a probe 20 as grasped by a user during a fetal cerebral oxygenation measurement procedure. The probe 20 may comprise a probe head 22 having a shape as illustrated in FIGS. 12A-12B, wherein the top portion 51 and the bottom portion 53 of the housing comprise different shapes. The probe head 22 can be grasped between the index and middle fingers of the user, with the distal portions of the fingers engaging a groove 29 in the housing of the head as described herein. The cable bundle 24 can be run along the inside of the hand, as shown in FIGS. 13B and 13C. The head 22 may be compactly sized to easily fit within the distal portions of the user's fingers. For example, the length 70 from the tip of the head 22 to the end of the strain relief element 40 may be about 40 mm, as shown in FIG. 13A. The bottom portion 53 of the housing of the head may have a thickness 71 of about 10 mm, as shown in FIG. 13B. The diameter D of the bottom portion of the housing may be about 18 mm to about 20 mm, as shown in FIG. 13C.

Figure 14A:
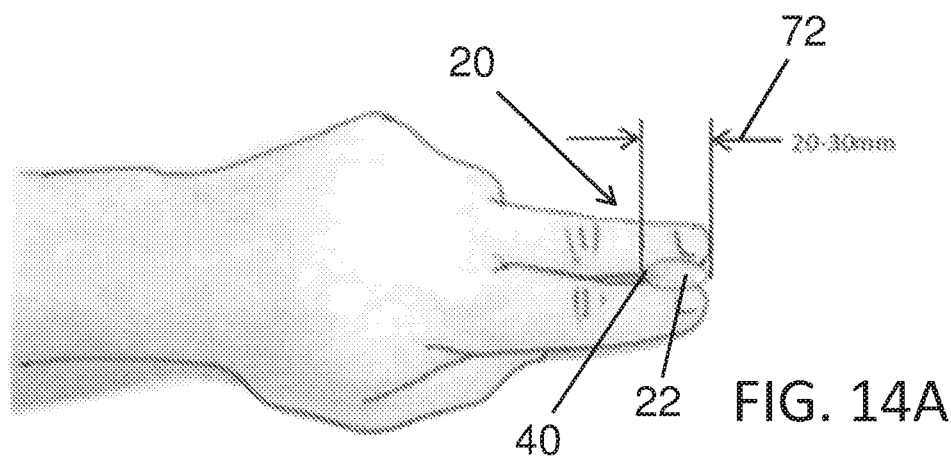
FIGS. 14A, 14B, and 14C illustrate another probe as grasped by a user during a fetal cerebral oxygenation measurement procedure, according to many embodiments.
Figure 14B:
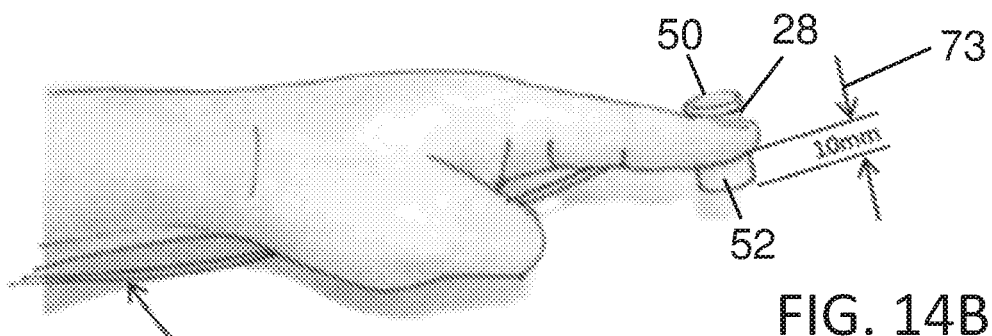
Figure 14C:
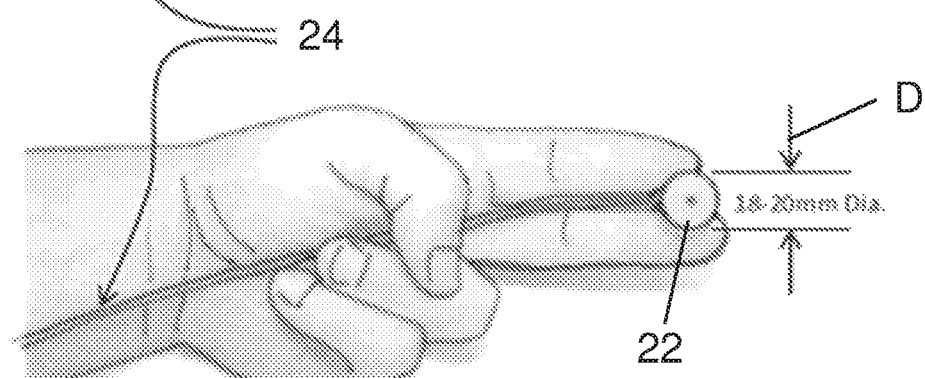

FIGS. 14A-14C illustrate another exemplary configuration of a probe 20 as grasped by a user during a fetal cerebral oxygenation measurement procedure. The probe 20 may comprise a probe head 22 having a shape as illustrated in FIGS. 11A-11B, wherein the top portion 50 and the bottom portion 52 of the housing comprise substantially the same circular shape. The probe head 22 can be grasped between the index and middle fingers of the user, with the distal portions of the fingers engaging a groove 28 in the housing of the head as described herein. The cable bundle 24 be run along the inside of the hand, as shown in FIGS. 14B and 14C. The head 22 may be compactly sized to easily fit within the distal portions of the user's fingers. For example, the length 72 from the tip of the head 22 to the end of the strain relief element 40 may be about 20 mm to about 30 mm, as shown in FIG. 14A. The bottom portion 52 of the housing of the head may have a thickness 73 of about 10 mm, as shown in FIG. 14B. The diameter D of the bottom portion of the housing may be about 18 mm to about 20 mm, as shown in FIG. 14C.

Figure 15A:
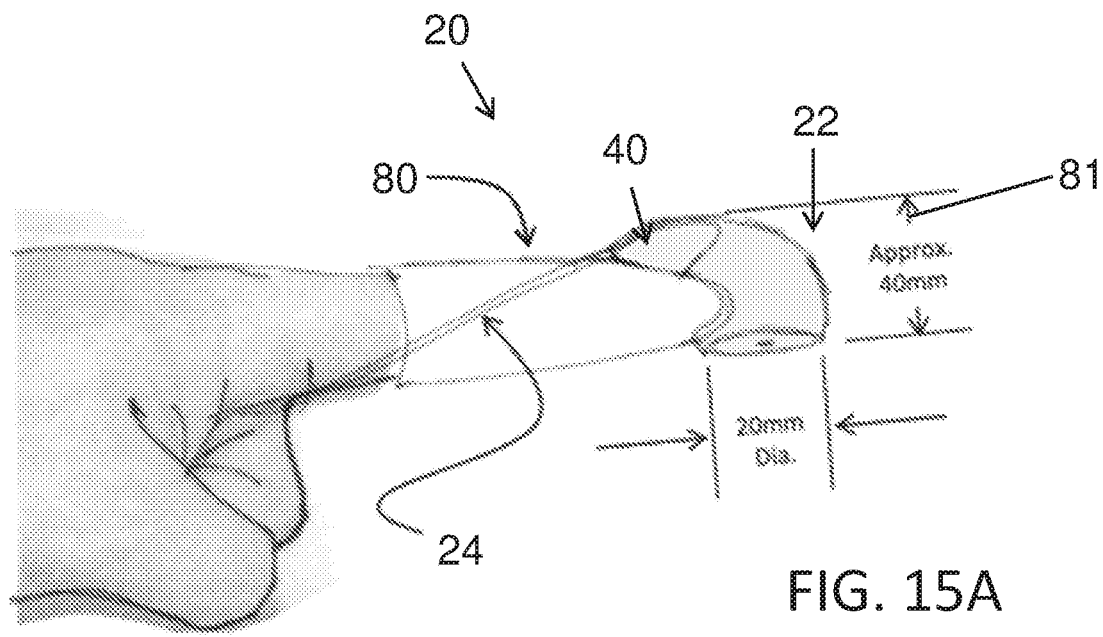
FIGS. 15A and 15B illustrate yet another probe as grasped by a user during a fetal cerebral oxygenation measurement procedure, according to many embodiments.
Figure 15B:
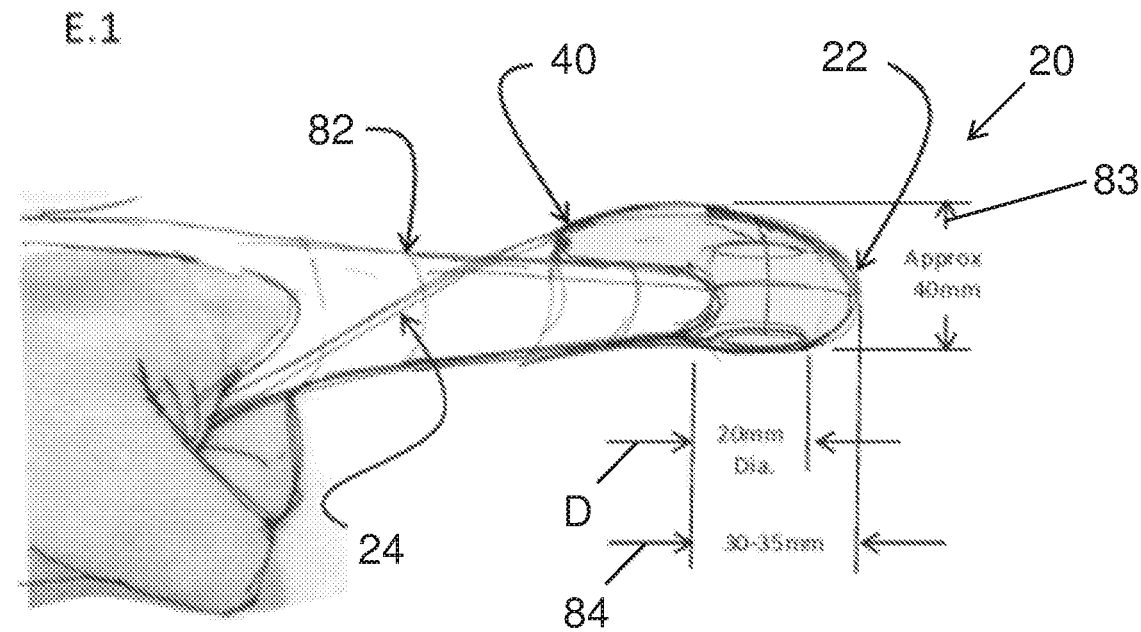

FIGS. 15A and 15B illustrate another exemplary configuration of a probe 20 as grasped by a user during a fetal cerebral oxygenation measurement procedure. The probe 20 may comprise a probe head 22 and strain relief element 40 as described herein, wherein the head 22 may comprise a housing having a groove, such as groove 28 or 29 as shown in FIGS. 11B and 12B. The user may grasp the head 22 with two fingers as described herein, or the user may place the tip of a single finger within the groove. As shown in FIG. 15A, a finger cot 80 may be placed over the one or two fingers engaging the head 22, in order to securely couple the head to the one or two fingers of the user. The head 22 disposed within the finger cot 80 may have a height 81 of about 40 mm, with the bottom portion of the housing having a diameter D of about 20 mm. A portion of the cables 24, extending out of the strain relief element 40, may be enclosed within the finger cot 80, with the remainder of the cable configured to be run along the inside of the hand. Alternatively, as shown in FIG. 15B, a finger glove 82 may be placed over the one or two fingers of the user engaging the probe head 22, wherein the finger glove may have straps that are secured around the wrist of the user in order to securely couple the finger glove to the user's hand. To facilitate insertion of the finger and the probe head into the finger glove 82 or finger cot 80, the probe head 22 may comprise a tapered "bull-nose" shape on the tip of the head, as shown in FIG. 15B. The strain relief 40 may also comprise a tapered bull-nose shape, so as to further relieve tension placed on the cables 24. The housing of the probe may comprise the bull-nose shape as shown, or alternatively, an adaptor may be placed over the housing to provide the bull-nose shape. The bull-nose shaped probe head 22 of FIG. 15B can have a height 83 of about 40 mm, a bottom diameter D of about 20 mm, and a maximum diameter 84 of about 30 mm to about 35 mm.

Figure 17A:
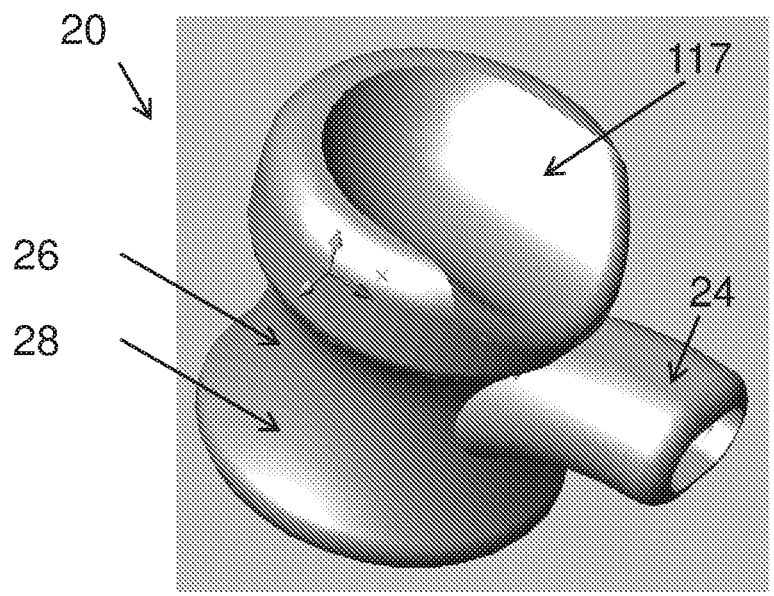
FIGS. 17A, 17B, and 17C illustrate an exemplary configuration of an optoacoustic probe, according to many embodiments.
Figure 17B:
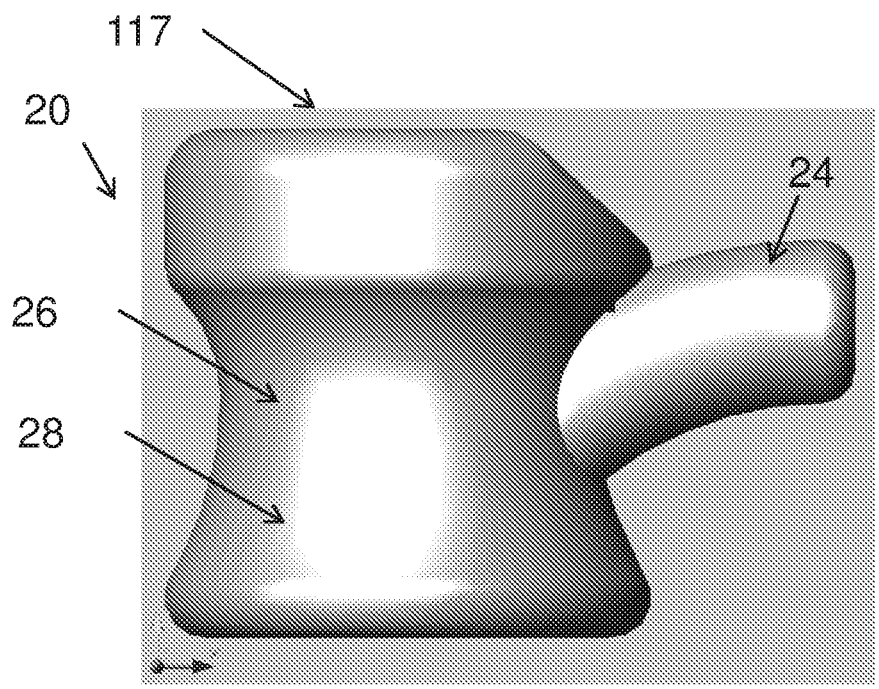
Figure 17C:
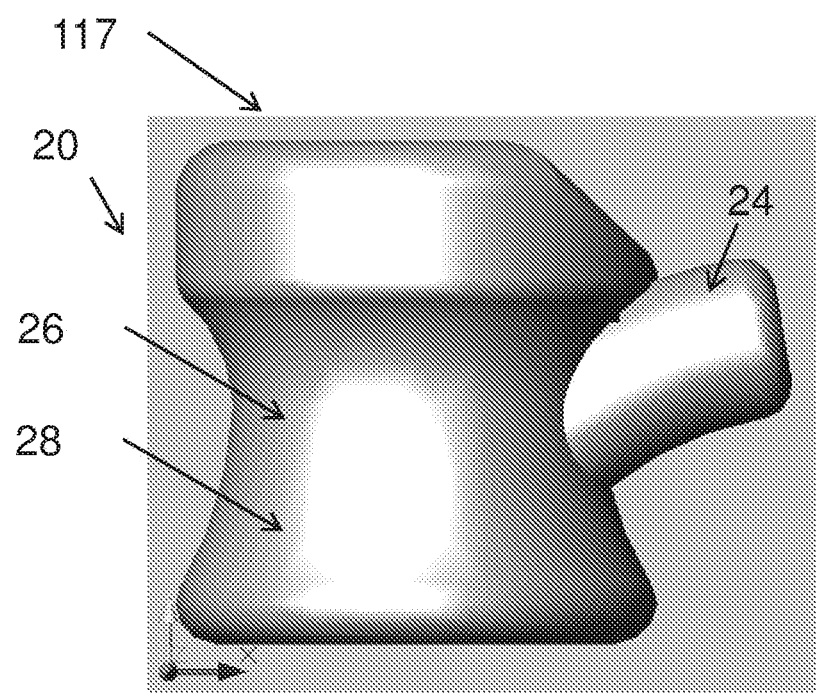

FIGS. 17A-17C show a further embodiment of the probe 20. In this embodiment, the probe 20 may comprise a housing 26 which may include a continuous rounded groove 28 that encircles the center of the housing 26. The housing 26 may further comprise a finger pocket 117 where a user can place his or her finger to manipulate and position the probe 20 while using another finger to palpate for the SSS or fontanel on the fetus. The finger pocket 117 may be located on one end of the probe 20 while the light output and acoustic transducer is located on the other end as described above and herein. The cables 24 may extend in a straight manner proximally from the housing 26 (FIG. 17B) or at an angle (FIG. 17C).

Figure 16:
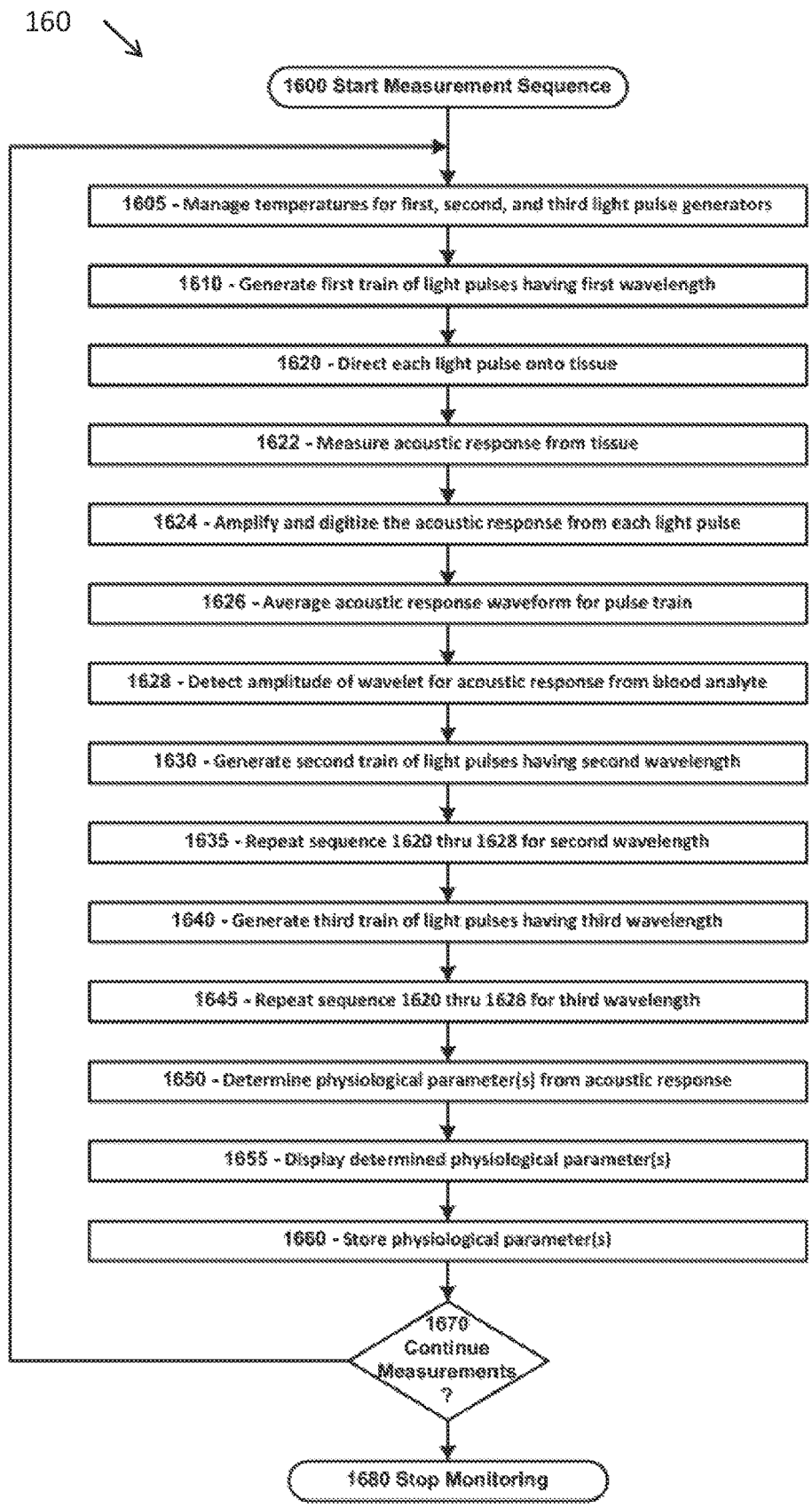
FIG. 16 shows a flowchart of an exemplary method to measure or detect one or more physiological parameters optoacoustically, according to many embodiments.

FIG. 16 shows a flowchart of a method 160 of determining one or more physiological parameters optoacoustically.

In a step 1600, a measurement sequence may be started.

In a step 1605, the temperatures of the first, second, and third light pulse generators may be managed as described above and herein. For example, the temperatures may be managed to keep the light pulse generators in an optimal temperature range for operation, for example, 10° C. to 40° C. The first, second, and third light pulse generators may comprise laser diodes (for example, laser diodes 152A1, 152B1, and/or 152B1 described above) for which the stability of the light output frequency is dependent on temperature. The step 1605 may comprise sub-steps of continuously measuring the temperatures of the first, second, and third light pulse generators; directing a cooling air current (from cooling fan 160, for example) to the first, second, and third light pulse generators; activating first, second, and third thermoelectric coolers (for example, thermoelectric coolers 152A2, 152B2, and/or 152C2 described above) coupled to the first, second, and third light pulse generators, respectively, to direct heat away from the first, second, and third light pulse generators; and, adjusting the cooling air current and thermoelectric coolers to maintain the first, second, and third light pulse generators in the optimal, operational temperature range. In a step 1610, a first light pulse train may be generated as described above and herein, and the first light pulse train may have a first wavelength.

In a step 1620, each light pulse of the generated pulse train may be directed onto tissue as described above and herein. The generated light pulses may be directed onto the tissue of interest such as with a patient interface device, for example, the patient interface 150 described above and/or the optoacoustic probe 14. The step 1610 may comprise sub-steps of providing the handheld probe 20 and positioning the probe 20 adjacent the tissue of interest to be interrogated such as the anterior fontanel of a fetus as described above).

In a step 1622, the acoustic response from the tissue can be measured as described above and herein. The acoustic response may comprise the acoustic response of the superior sagittal sinus of the fetus as described above. As described above, for example, the acoustic response may be captured with an acoustic sensor 56 of the probe 20 or other effector portion of the patient interface 150.

In a step 1624, the acoustic response from each light pulse may be amplified and digitized as described above and herein. As described above, for example, the electrical signals generated by the acoustic sensor 56 may be amplified with a preamplifier of the probe 20. The preamplified signals may be received by the acoustic subsystem 140 of the console unit 100. The preamplified signals may then be further amplified by the acoustic subsystem 140 and then sampled with a digitizer. The sampled signals may then be transferred to the processor 115 of the console 110 for waveform averaging to extract the waveform out of background noise.

In a step 1626, the acoustic response waveform for the pulse train may be averaged as described above and herein.

In a step 1628, the amplitude of the wavelet for the acoustic response from the blood analyte can be detected as described above and herein.

In a step 1630, a second light pulse train may be generated as described and herein, and the second light pulse train may have a second wavelength different from the first wavelength.

In a step 1635, the steps 1620 through 1628 may be repeated for the second wavelength.

In a step 1640, a third light pulse train may be generated as described and herein, and the third light pulse train may have a third wavelength different from the first and second wavelengths.

In a step 1645, the steps 1620 through 1628 may be repeated for the second wavelength. As described herein and above, the first, second, and third wavelengths may be different from one another and may be selected to match the absorption peak and acoustic response peak of the target parameter of interest. As described herein and above, exemplary wavelengths include 700 nm, 730 nm, 760 nm, 800 nm, 805 nm, and 860 nm, to name a few. For example, the first wavelength may be 800 nm or 805 nm, the isosbestic point where oxyhemoglobin and deoxyhemoglobin have equal absorption and the second and third wavelengths may be wavelengths where oxyhemoglobin and deoxyhemoglobin have strong differences in absorption such as 700 nm, 730 nm, and 760 nm.

In a step 1650, the physiological parameter(s) may be determined from the acoustic response. The processor 115 of the console unit 100 may be configured to make such a determination. For example, the physiological parameter(s) of interest, such as blood oxygenation or SSS($SO_2$), may be determined by comparing the acoustic response at two different wavelengths of the light pulses. To provide a more accurate and reliable reading of the physiological parameter(s) of interest, two or more of the determined physiological parameter(s) may be averaged together as described herein.

In a step 1655, the determined physiological parameter(s) may be displayed as described above and herein, such as with a display 125 of the console unit 100 as described above. In some embodiments, the averaged physiological parameter(s) are displayed.

In a step 1660, the determined physiological parameter(s) may be stored in a memory. For example, the physiological parameter(s) measured may be electronically sent to an electronic health record management system by the console unit 100.

In a step 1670, the user may be queried as to whether to continue measurements. If the user desires to continue the measurements, the measurement sequence may be restarted with the step 1600. In the user desires to end the measurements, the measurement sequence may be stopped with the step 1680. It can be determined whether further steps are necessary may be determined. For example, a physician or other medical professional can make a determination of whether a caesarian procedure is necessary based on the measured blood oxygenation shown by the console unit 100. Alternatively or in combination, the console unit 100 may be configured to make and show a recommendation as to whether a caesarian or other procedure is necessary based on the measured blood oxygenation shown.

Although the above steps show the method 160 of determining one or more physiological parameters optoacoustically in accordance with many embodiments, a person of ordinary skill in the art will recognize many variations based on the teaching described herein. The steps may be completed in a different order. Steps may be added or deleted. For example, oxygenation or other physiological parameter of interest may be determined using pulse trains of light at two or fewer wavelengths. Some of the steps may comprise sub-steps. Many of the steps may be repeated as often as beneficial to the diagnostic measurement(s).

One or more of the steps of the method 160 may be performed with various circuitry, as described herein, for example one or more of the processor, controller, or circuit board described above and herein. Such circuitry may be programmed to provide one or more steps of the method 1600, and the program may comprise program instructions stored on a computer readable memory or programmed steps of the logic circuitry such as programmable array logic or a field programmable gate array, for example.

Aspects of the present disclosure also include methods of measuring oxygenation. Such methods include the application of formulas to measure oxygenation when signals are good (i.e., there is low background). Exemplary formulas to determine blood oxygenation at different wavelengths of light signals are listed below, where R is the ratio of optoacoustic amplitudes at 760 and 800 nm (R=$A_{760}/A_{800}$).

$$760 \text{ nm}: SO_2 = 1.54 - 0.76 \cdot R \rightarrow R = 2.02 - 1.31 \cdot SO_2$$

$$850 \text{ nm}: SO_2 = -2.42 + 2.66 \cdot R \rightarrow R = 0.91 + 0.38 \cdot SO_2$$

In general, for any wavelength: $R = a'_i + b'_i \cdot SO_2$

For instance, introducing 1.0 to generate a difference of signals would yield:

$$R - 1 = a_i + b_i \cdot SO_2 - 1$$

$$\frac{A_{760}}{A_{800}} - 1 = a_i + b_i \cdot SO_2 - 1$$

And, the differential signal $D_{760} = A_{760} - A_{800}$ may be represented by the equation:

$$\frac{A_{760} - A_{800}}{A_{800}} = b'_i SO_2 + a'_i \cdot \cdot 1 = -1.31 \times SO_2 + 2.02 - 1 = -1.31 \cdot SO_2 + 1.02$$

So, in general, for any wavelength, the below equation (Eq. 1) may apply:

$$\frac{A_i - A_{800}}{A_{800}} = b'_i SO_2 + a'_i \cdot \cdot 1$$

And, a third wavelength (e.g. 850 nm) may be introduced to remove $A_{800}$ as follows with the following equation (Eq. 2):

$$\frac{A_{850} - A_{800}}{A_{800}} = 0.38 \cdot SO_2 + 0.91 - 1 = 0.38 \cdot SO_2 - 0.09$$

To remove $A_{800}$, Eq. 1 may be divided by Eq. 2 as follows.

$$RDS \equiv \frac{A_{760} - A_{800}}{A_{850} - A_{800}} = \frac{-1.31 \cdot SO_2 + 1.02}{0.38 \cdot SO_2 - 0.09}$$

$(0.38 \cdot SO_2 - 0.09) \cdot (A_{760} - A_{800}) = (-1.31 \cdot SO_2 + 1.02) \cdot (A_{850} - A_{800})$ And where $D_{760} = A_{760} - A_{800}$ and $D_{850} = A_{850} - A_{800}$ $0.38 \cdot D_{760} \cdot SO_2 - 0.09 \cdot D_{760} = -1.31 \cdot D_{850} \cdot SO_2 + 1.02 \cdot D_{850}$ $0.38 \cdot D_{760} \cdot SO_2 + 1.31 \cdot D_{850} \cdot SO_2 = 1.02 \cdot D_{850} + 0.09 \cdot D_{760}$ $SO_2(0.38 \cdot D_{760} + 1.31 \cdot D_{850}) = 1.02 \cdot D_{850} + 0.09 \cdot D_{760}$ $$SO_2 = \frac{1.02 \cdot D_{850} + 0.09 \cdot D_{760}}{0.38 \cdot D_{760} + 1.31 \cdot D_{850}}$$

The last above equation for $SO_2$ can be used to measure oxygenation using any (bad or good) signals with high background from hair or skin melanin, for instance, (such as in fetuses, neonatal and adult heads, and dark skin). Therefore, three or more wavelengths of light signals or two or more wavelength pairs for light signals may be used to measure oxygenation optoacoustically, even in conditions of high background. The wavelengths noted above are examples only, and other wavelengths are also contemplated for use as described above and herein. The above coefficients for the various formulas and equations are examples only as well, and other coefficients for the above formulas and equations are also contemplated for use.

Experimental Data

In an experimental procedure, hemodynamically stable neonates were optoacoustically measured in order to simulate optoacoustic monitoring of a fetus. An optical parametric oscillator (OPO) was controlled by a personal computer that was programmed to rapidly switch between three wavelengths: 800 nm (isobestic point), 760 nm, and 700 nm at an energy level of 15 microjoules, similar to the energy produced by pulsed laser diodes. $SSS(SO_2)$ was then calculated from each of two pairs of wavelengths (760 nm and 800 nm) and (700 nm and 800 nm) and then the mean of the two calculations was determined. By taking the mean of two or more calculations, a more accurate measurement of blood oxygenation can be made.

Figure 10A:
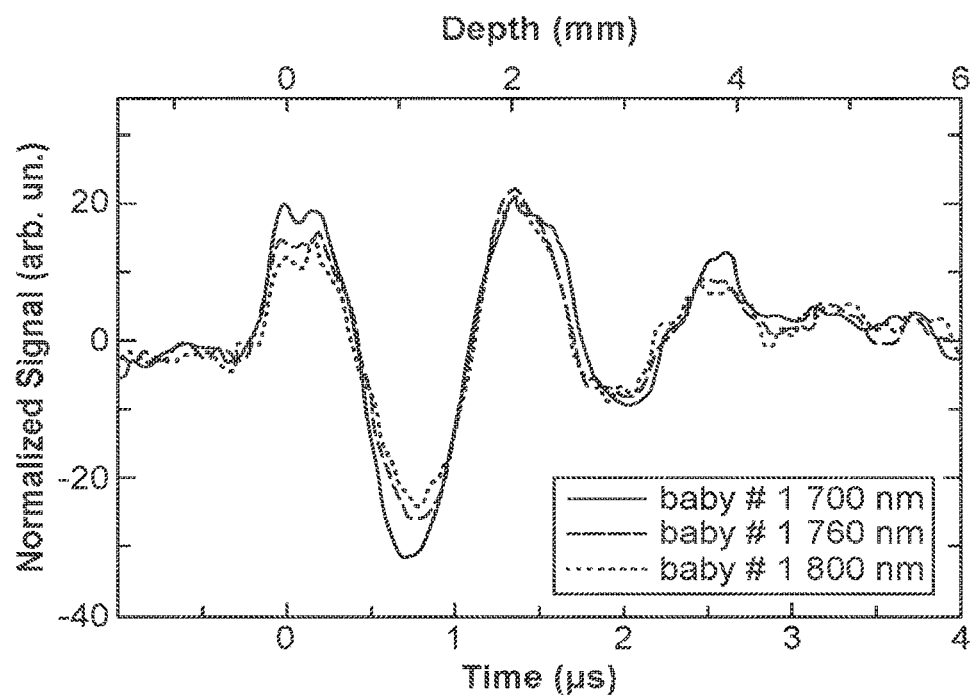
FIG. 10A is a graph that plots optoacoustic signals recorded from the superior sagittal sinus (SSS) of a first baby at various wavelengths, according to many embodiments.
Figure 10B:
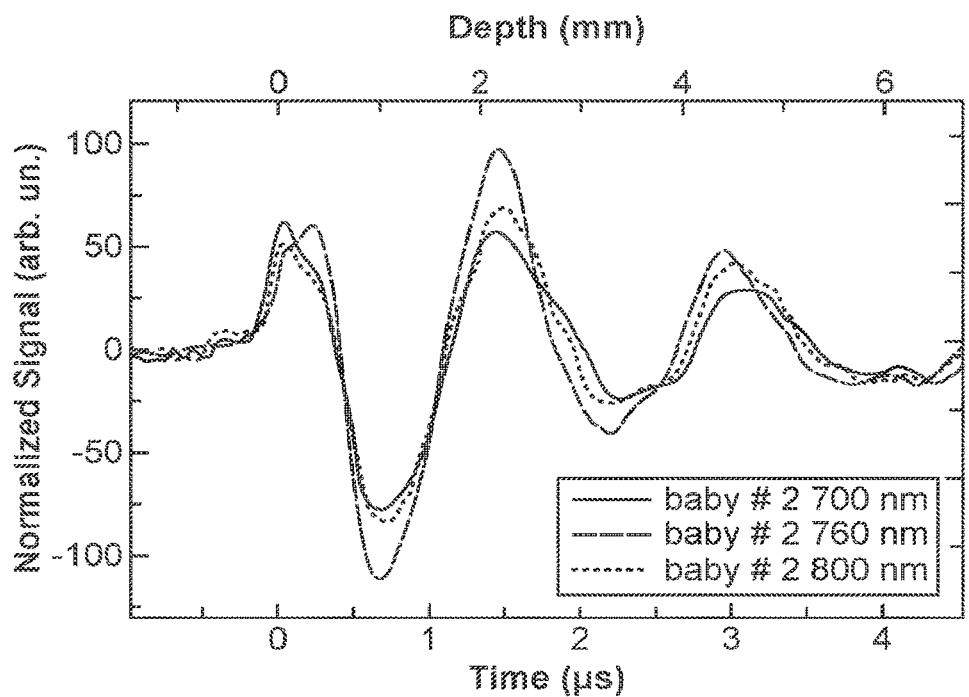
FIG. 10B is a graph that plots typical optoacoustic signals recorded from the SSS of a second baby at various wavelengths, according to many embodiments.

In the first of two neonates (Baby 1: weight 1,795 g; current weight 2,885 g; gestational age 32 wks), at two time intervals, $SSS(SO_2)$ was 58% and 69%. In the second neonate (Baby 2: weight 3,040 g; gestational age 39 wks), at three time intervals, $SSS(SO_2)$ was 55%, 60%, and 62%. These measurements are consistent with the expected ranges and with physiologic changes over time. FIGS. 10A and 10B show the raw data from which $SSS(SO_2)$ was calculated for Babies 1 and 2.

While measurements at three different wavelengths can be taken, it is noted that measurements can be taken at other numbers of wavelengths. For example, in some embodiments, measurements can be taken at 760 nm and 800 nm. Furthermore, while the optoacoustic probe described herein comprises an optical waveguide that turns light generated by a light source through 90°, it is noted that the light can be emitted from the probe at any angle from 0° (i.e., straight from the tip of the probe) to 90°. The particular angle that is used may depend upon which angle provides the easiest access to the fetal head and fontanel depending upon fetal head position and anatomy.

Figure 18A:
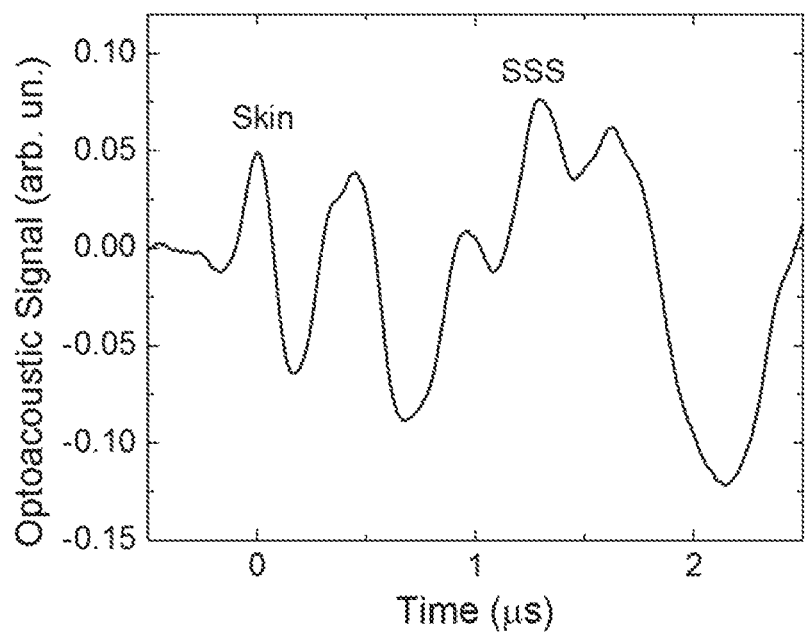
FIG. 18A is a graph that plots differential optoacoustic signals recorded from a fetus during late stage labor, according to many embodiments.
Figure 18B:
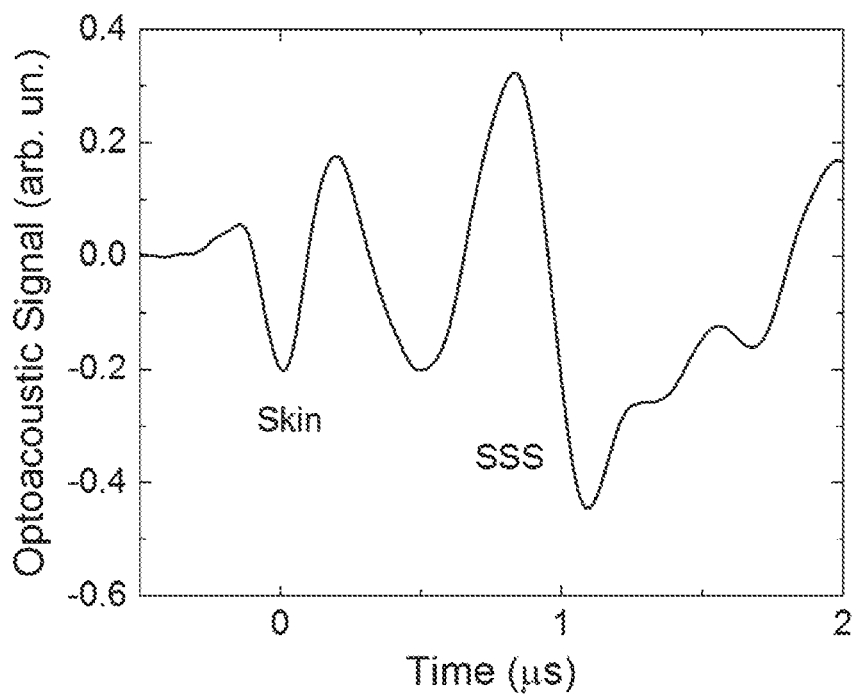
FIG. 18B is a graph that plots differential optoacoustic signals recorded from a fetus during late stage labor, according to many embodiments.

In another experimental procedure, acoustic signals were measured from a fetus during late stage labor. The acoustic response was generated by directing light signals to tissue at 760 nm, 800 nm, and 850 nm. FIG. 18A shows a measured differential signal where the signal obtained at 800 nm was subtracted from the signal obtained at 760 nm. FIG. 18B shows a measured differential signal where the signal obtained at 800 nm was subtracted from the signal obtained at 850 nm. The two peaks shown in each graph may represent the acoustic response from skin and the acoustic response from the superior sagittal sinus (SSS). The peak from the SSS may be used to determine the venous oxygenation of the fetus at the SSS.

While preferred embodiments of the present disclosure have been shown and described herein, it will be obvious to those skilled in the art that such embodiments are provided by way of example only. Numerous variations, changes, and substitutions will now occur to those skilled in the art without departing from the scope of the present disclosure. It should be understood that various alternatives to the embodiments of the present disclosure described herein may be employed in practicing the inventions of the present disclosure. It is intended that the following claims define the scope of the invention and that methods and structures within the scope of these claims and their equivalents be covered thereby.

We claim:

1. A desktop-sized console for measuring hemoglobin concentration in a subject, said console comprising:
    a laser diode subsystem for emitting light pulses directed to tissue of a subject, the laser diode subsystem comprising:
        a first laser diode configured to emit a first light pulse at a first output wavelength in a range of 790 nm to 820 nm,
        a first thermoelectric cooler coupled to the first laser diode to regulate a temperature of the first laser diode,
        a first cooling fan, and
        at least one controller coupled to and configured to control the first cooling fan and the first thermoelectric cooler to regulate the temperature of the first laser diode to stabilize the output wavelength of the first laser diode within an optimal range;
    an acoustic sensor subsystem for measuring acoustic pressure generated in the tissue in response to the emitted light pulse; and
    a processor coupled to the laser diode subsystem to control the laser diode subsystem and coupled to the acoustic sensor subsystem to receive the measured acoustic pressure, wherein the processor is configured to determine hemoglobin concentration of the subject in response to the received acoustic pressure.

2. The console of claim 1, wherein the laser diode subsystem further comprises a second laser diode configured to emit a second light pulse at a second output wavelength different from the first output wavelength and a second thermoelectric cooler coupled to the second laser diode to regulate a temperature of the second laser diode, and wherein the at least one controller is further coupled to the second thermoelectric cooler to regulate the temperature of the second laser diode and to stabilize the output wavelength of the second laser diode within an optimal range.

3. The console of claim 2, wherein the laser diode subsystem further comprises a third laser diode configured to emit a third light pulse at a third output wavelength different from the first and second output wavelengths and a third thermoelectric cooler coupled to the third laser diode to regulate a temperature of the third laser diode, and wherein the at least one controller is further coupled to the third thermoelectric cooler to regulate the temperature of the third laser diode and to stabilize the output wavelength of the third laser diode within an optimal range.

4. The console of claim 3, wherein the laser diode subsystem further comprises a first temperature sensor to measure the temperature of the first laser diode, a second temperature sensor to measure the temperature of the second laser diode, and a third temperature sensor to measure the temperature of the third laser diode, and wherein the at least one controller is configured to regulate the temperatures of the first, second, and third laser diodes in response to the temperatures measured by the first, second, and third temperature sensors.

5. The console of claim 3, wherein the first, second, or third wavelength is at an isosbestic point of oxyhemoglobin and deoxyhemoglobin.

6. The console of claim 1, wherein the laser diode subsystem further comprises a first temperature sensor to measure the temperature of the first laser diode, and wherein the controller is configured to regulate the temperatures of the first laser diode in response to the temperatures measured by the first temperature sensor.

7. The console of claim 1, wherein the first wavelength is at an isosbestic point of oxyhemoglobin and deoxyhemoglobin.

8. The console of claim 1, further comprising a power supply coupled to the laser diode subsystem, the acoustic sensor subsystem, and the processor.

9. The console of claim 1, further comprising a display coupled to the processor to display the determined hemoglobin concentration to a user.

10. The console of claim 9, wherein the display comprises a touch screen for operating the console.

11. The console of claim 1, further comprising a desktop-sized housing enclosing the laser diode subsystem, the acoustic sensor subsystem, and the processor.

12. The console of claim 11, further comprising a second cooling fan coupled to one or more of the processor or acoustic sensor subsystem for cooling the console.

13. The console of claim 1, wherein the processor is further configured to read or write to medical records of the subject.

14. The console of claim 1, further comprising an output port for the laser diode subsystem and an input port for the acoustic sensor subsystem.

15. The console of claim 14, wherein the output port and the input port are configured to be coupled to a sensor module or an optoacoustic probe to emit the first light pulse to the tissue of the subject and to receive the acoustic pressure generated in the tissue.

16. The console of claim 15, wherein the output port and the input port are configured to be coupled to the sensor module or optoacoustic probe with a cable comprising one or more optical fibers.

* * * * *